United States Patent [19]
Chabrecek et al.

[11] Patent Number: 6,099,122
[45] Date of Patent: Aug. 8, 2000

[54] PROCESS FOR THE FUNCTIONALIZATION OF SURFACES

[75] Inventors: Peter Chabrecek, Clayton, Australia; Dieter Lohmann, Münchenstein, Switzerland

[73] Assignee: CIBA Vision Corporation, Duluth, Ga.

[21] Appl. No.: 08/860,130

[22] PCT Filed: Dec. 18, 1995

[86] PCT No.: PCT/EP95/05013

§ 371 Date: Aug. 18, 1997

§ 102(e) Date: Aug. 18, 1997

[87] PCT Pub. No.: WO96/20796

PCT Pub. Date: Jul. 11, 1996

[30] Foreign Application Priority Data

Dec. 30, 1994 [CH] Switzerland ............... 3967/94

[51] Int. Cl.[7] .................................................. G02C 7/04
[52] U.S. Cl. ........................................ 351/160 H; 351/177
[58] Field of Search ..................... 351/160 H, 160 R, 351/161, 162, 177

[56] References Cited

U.S. PATENT DOCUMENTS 5,527,925  6/1996  Chabrecek et al. ............... 549/430
5,532,112  7/1996  Koehler et al. .................... 430/281.1

FOREIGN PATENT DOCUMENTS

| B12624 | 3/1988 | Australia . |
|---|---|---|
| 0281941 | 3/1988 | European Pat. Off. . |
| 0574352A1 | 6/1993 | European Pat. Off. . |
| 0632329A1 | 7/1993 | European Pat. Off. . |

*Primary Examiner*—Scott J. Sugarman
*Attorney, Agent, or Firm*—R. Scott Meece; Robert J. Gorman, Jr.

[57] ABSTRACT

The present invention describes a novel coating process that comprises the use of a functional photoinitiator, or a macroinitiator derived therefrom, in a cascade of process steps, wherein, on the one hand, a functional photoinitiator or a macroinitiator derived therefrom is covalently bonded to a carrier and, on the other hand, an oligomer or polymer forming a new surface layer is covalently bonded to the functional photoinitiator, or to the carrier modified by a functional photoinitiator, via functional groups that are co-reactive with isocyanate groups. The invention relates also to novel intermediates that are carriers to which functional photoinitiators that contain free isocyanate groups are bonded.

17 Claims, No Drawings

PROCESS FOR THE FUNCTIONALIZATION OF SURFACES

BACKGROUND OF THE INVENTION

The present invention relates to a novel coating process that comprises the use of a functional photoinitiator, or a macroinitiator derived therefrom, in a cascade of process steps, wherein, on the one hand, a functional photoinitiator or a macroinitiator derived therefrom is covalently bonded to a carrier and, on the other hand, an oligomer or polymer forming a new surface layer is covalently bonded to the functional photoinitiator, or to the carrier modified by a functional photoinitiator, via functional groups that are co-reactive with isocyanate groups. The invention relates also to novel intermediates that are carriers to which functional photoinitiators that contain free isocyanate groups are bonded.

The surface-modification of polymers has been the focus of interest for many years. The properties of a polymer often have to satisfy various physical and chemical requirements which, because of the material used, can often be met only in part. One possible way of meeting those requirements is to cover a base material with a thin layer of a second material. The latter should supply the properties lacking in the first material but not alter the fundamental properties of the base material. Special attention is paid in this connection to improved bio-compatibility in the widest sense, for example to the wettability of polymer surfaces.

A pioneering work in the field of surface-modification of polymers, aimed at improving specifically the wettability of the surfaces of contact lenses, has come from Yasuda et al., J. Biomed. Mater. Res. 9, 629 (1975). The authors describe a process in which a layer of 20 nm thickness is applied by plasma polymerisation of a mixture of acetylene, water and nitrogen to a PMMA contact lens. The plasma is produced in an apparatus for downstream coating, with a high-frequency glow discharge and an operating frequency of 13.56 MHz. The contact angle of a normal, untreated PMMA surface is, according to the standing water droplet method, approximately 71° and, after the plasma polymerisation coating just described, approximately 37°.

Another attractive method for applying thin hydrophilic films to substrates is to use unsaturated alcohols in the plasma polymerisation. Hozumi et al., Pure & Appl. Chem. 60, 697 (1988), describe a high-frequency glow discharge method in which they employ allyl alcohol and propargyl alcohol, and also 2-methyl-3-butyn-2-ol. The tests, carried out mainly with propargyl alcohol, show that a contact angle of 45° results after the coating. If, in addition, water is added to the operating gas in the plasma polymerisation, the contact angle can even be reduced to 20°. When a product so coated is swelled with water, however, it is found that the additional layer exhibits unsatisfactory adhesion to the substrate.

Two more recent publications, PCT-AU 89/00220 and H. J. Griesser, Materials Forum, 14 (1990) 192, deal with a plasma polymerisation method in which organic compounds, such as saturated alcohols, saturated amines, derivatives or mixtures thereof, and inorganic gases, such as oxygen, hydrogen, nitrogen, helium, argon or neon, and water vapour are applied as a plasma polymer to a contact lens. According to the authors, the water content should lie between a maximum of 20% by volume and preferably 5% by volume. The presence of water is intended to prevent excessive crosslinking of the plasma polymer. Examples are given in which films are applied by plasma polymerisation of ethanol and isobutanol. During the glow discharge, the substrates are subjected to an energy of approximately 1 watt/cm$^2$ between two plane-parallel electrodes. If a sufficiently high static potential occurs on those substrates, spontaneous, high-energy discharges are released which greatly heat the substrate and cause internal stresses. As a result, plasma polymer deposits that are highly crosslinked and difficult to control are produced.

WO 94/06485 describes a multi-layer material, especially a biomedical article and preferably a contact lens, having one or more wettable surfaces capable of holding an intact film of aqueous fluid, the multi-layer material consisting of a base material and a hydrophilic layer, and the hydrophilic layer being formed by a carbohydrate derivative that is covalently bonded to reactive groups on the surface of the base material either directly or indirectly via functional groups of a further oligofunctional compound which is laid between the base material and the hydrophilic layer and covalently bonded on both sides.

By the specific use of suitable functional photoinitiators in a multi-stage coating process it has now become possible accurately to control the nature of the applied layers by different reaction mechanisms, namely photo-chemical and chemical reaction mechanisms. The use of functional photoinitiators makes it possible to produce firmly bonded surface layers of high uniformity, layer thickness, coating density and durability.

EP-A-632 329 already describes functional photoinitiators that are also employed according to the present invention. According to that prior art, however, the photoinitiators are always used in such a way that first the isocyanate group thereof reacts with co-reactive groups of the substrate surface. The attachment of oligomers or polymers forming a new surface is then effected by way of radicals by means of the photoinitiator part.

SUMMARY OF THE INVENTION

In contrast, the process according to the invention takes a different route inasmuch as although, on the one hand, a functional photoinitiator or a macroinitiator derived therefrom is also covalently bonded to a carrier, on the other hand the oligomer or polymer forming a new surface layer is bonded to the carrier modified by a functional photoinitiator via groups that are co-reactive with isocyanate groups.

Although photoinitiators are also bonded to surfaces according to EP-A-632 329, the new surfaces on a carrier can be formed in the last process step only by ethylenically unsaturated, photo-polymerisable or photo-crosslinkable substances. In contrast, the present invention makes it possible, after photochemical functionalisation of the surface using functional photoinitiators, to produce a new surface using a large number of known, prefabricated synthetic oligomers or polymers or biomaterials that carry H-active groups.

The present invention therefore relates to a novel coating process which comprises, on the one hand, covalently bonding a functional photoinitiator containing at least one isocyanate group, or a macroinitiator derived therefrom, to a carrier and, on the other hand, covalently bonding an oligomer or polymer, forming a new surface layer, to the functional photoinitiator or to the carrier modified by a functional photoinitiator via functional groups that are co-reactive with isocyanate groups. The functional photoinitiator is preferably a compound of formula Ia or Ib. Macroinitiators derived therefrom are also described hereinafter. The process according to the invention is preferably applied to the surface of a biomedical article, a textile or an industrial moulded article, especially to the surface of an ophthalmic moulded article, for example a contact lens.

As a result of such a coating, hydrophilic, water-repellent, slidable, colorable, anti-fouling and bio-compatible surfaces, for example, are produced on an inorganic or organic base material. In addition, it is also possible to produce layers that provide the base material with a protection against wear, abrasion, corrosion, (photo-)oxidation, bio-erosion or undesirable deposits (such as dirt, proteins, lipids, salts, lime, microorganisms, cosmetics, chemicals, etc.) or that form a barrier against the ingress, migration or permeation of undesirable substances (gases, liquids or solids).

DESCRIPTION OF THE PREFERRED EMBODIMENT

The present invention relates preferably to a coating process that comprises the following steps:
(a) applying a thin layer of a functional photoinitiator of formula Ia or Ib to a surface containing suitable groups that are co-reactive with radicals;
(b) irradiating the coated surface with UV light of a suitable wavelength, there being produced by radical α-cleavage in the functional photoinitiator benzoyl-like radicals that form a covalent bond with the co-reactive groups of the surface, while the isocyanate groups of the photoinitiators are preserved;
(c) applying to the surface modified by a photoinitiator an oligomer or polymer containing groups that are co-reactive with isocyanate groups;
(d) a covalent bond being formed by the oligomer or polymer with the isocyanate groups of the photoinitiators covalently bonded to the surface.

The present invention also relates preferably to a coating process that comprises the following steps:
(a) reacting an oligomer or polymer containing groups that are co-reactive with isocyanate groups with a functional photoinitiator of formula Ia or Ib to form a macroinitiator, the isocyanate group of the photoinitiator forming a covalent bond with one of the co-reactive groups of the oligomer or polymer,
(b) applying a thin layer of the macroinitiator so obtained to a surface containing suitable groups that are co-reactive with radicals;
(c) irradiating the coated surface with UV light of a suitable wavelength, there being produced by radical α-cleavage in the macroinitiator benzoyl-like radicals that form a covalent bond with the co-reactive groups of the surface.

The present invention preferably relates, in addition, to a coating process that comprises the following steps:
(a) where applicable providing the surface of a base material with functional groups that are co-reactive with isocyanate groups, for example OH, $NH_2$ or COOH, by suitable chemical or physical pre-treatment, for example plasma treatment;
(b) covering the surface containing groups that are co-reactive with isocyanate groups with a functional photoinitiator of formula Ia or Ib, the isocyanate group of the photoinitiator forming a covalent bond with the surface;
(c) covering the surface modified by a photoinitiator with a thin layer of a vinylic monomer containing at least one isocyanate group or a mixture of vinyl monomers containing such a monomer,
(d) irradiating the coated surface with UV light of a suitable wavelength, there being produced a graft (co)polymer containing isocyanate groups that is covalently bonded to the surface;
(e) applying to the surface so modified an oligomer or polymer containing groups that are co-reactive with isocyanate groups;
(f) a covalent bond being formed by the oligomer or polymer with the isocyanate groups of the graft (co)polymer.

The invention also relates to base materials that have been coated in accordance with the invention, especially films or ophthalmic moulded articles, for example contact lenses. These also include base materials that have been treated in accordance with the invention but do not possess the finally modified surface and that, rather, have been treated in accordance with the invention only as far as the stage where they still contain free isocyanate groups. These are, for example, base materials that are obtainable in accordance with claim 2 when only the steps (a) and (b) described therein are carried out, or when the steps (c) and (d) described therein are omitted, or base materials that are obtainable in accordance with claim 4 when only the steps (a) to (d) described therein are carried out, or when the steps (e) and (f) described therein are omitted.

Within the scope of the present invention, the term "carrier" is understood to mean a material that may be both a base material and a final surface material itself or a suitable intermediate layer. Examples of such carriers are glass, silica gels, ceramics, metal, wood, silicate minerals, metal oxides and, preferably, natural or synthetic oligomers or polymers of all kinds.

Natural oligomers and polymers are, for example, oligo- and poly-saccharides or derivatives thereof, peptides, proteins, glycoproteins, enzymes, antibodies and growth factors. Some examples are cyclodextrins, trehalose, cellobiose, lactose, lactosamine, lacto-biono-lactone, maltotriose, maltohexaose, chitohexaose, agarose, chitin 50, amylose, starch, hyaluronic acid, deacetylated hyaluronic acid, chitosan, glucanes, heparin, xylan, pectin, galactan, poly-galactosamine, glycosaminoglycanes, dextran, aminated dextran, cellulose, hydroxyalkylcelluloses, carboxyalkylcelluloses, fucoidan, chondroitin sulfate, sulfated polysaccharides, mucopolysaccharides, gelatin, zein, collagen, albumin, globulin, bilirubin, ovalbumin, keratin, fibronectin and vitronectin, pepsin, trypsin and lysozyme.

The synthetic oligomers and polymers may be, for example, polymers or hydrolysed polymers of vinyl esters or ethers (polyvinyl alcohol); polydiolefins or hydroxylated polydiolefins, e.g. polybutadiene, polyisoprene or polychloroprene or copolymers thereof; polyacrylic acid and polymethacrylic acid and also polyacrylates, polymethacrylates, polyacrylamides or polymethacrylamides, if desired having hydroxyalkyl or aminoalkyl radicals in the ester group or amide group; polysiloxanes, if desired having hydroxyalkyl or aminoalkyl groups; polyethers or aminated polyethers of epoxides or glycidyl compounds and diols; polyvinylphenols or copolymers of vinylphenol and olefinic comonomers; and copolymers of at least one monomer from the group vinyl alcohol, vinylpyrrolidone, acrylic acid, methacrylic acid, or hydroxyalkyl- or aminoalkyl-containing acrylates, methacrylates, or acrylamide or methacrylamide, or diolefms or hydroxylated diolefins with ethylenically unsaturated comonomers, e.g. acrylonitrile, olefins, diolefins, vinyl chloride, vinylidene chloride, vinyl fluoride, vinylidene fluoride, styrene, α-methylstyrene, vinyl ethers and vinyl esters; polyoxaalkylenes, if desired having pendant or terminal OH or aminoalkyloxy groups.

The expression "vinylic monomer containing at least one isocyanate group" is understood to mean especially an isocyanate that contains one or more lower alkenyl groups, for example an isocyanato-lower alkyl acrylate or methacrylate or styrene substituted by isocyanate or by isocyanato-lower alkyl, or an alkenyl isocyanate or alkenyloyl isocyanate, for example vinyl isocyanate, allyl isocyanate or acryloyl isocyanate.

By suitable choice of a carrier the properties of a surface, or of a material in general, can be controlled well. For example, a surface may be rendered hydrophilic or hydrophobic depending upon the required use. Other properties that can be imparted in that way are, for example, slidability, colorability, anti-fouling properties or bio-compatibility.

The functional photoinitiators used according to the invention are compounds of formula Ia or Ib

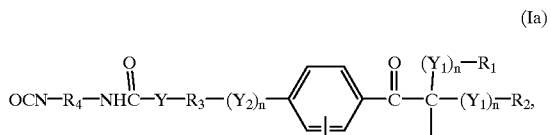
(Ia)

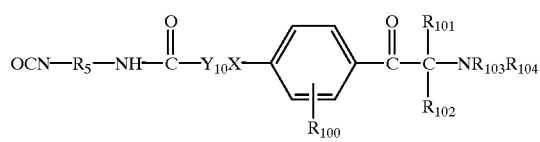
(Ib)

wherein Y is O, NH or $NR_{1A}$;

$Y_1$ is O;

$Y_2$ is —O—, —O—(O)C—, —C(O)—O— or —O—C(O)—O—;

each n independently of the other is 0 or 1;

R is H, $C_1$–$C_{12}$alkyl, $C_1$–$C_{12}$alkoxy or $C_1$–$C_{12}$alkylNH—;

$R_1$ and $R_2$ are each independently of the other H, linear or branched $C_1$–$C_8$alkyl, $C_1$–$C_8$-hydroxyalkyl or $C_6$–$C_{10}$aryl, or two groups $R_1$—$(Y_1)_n$— together are —$(CH_2)_x$—, or the groups $R_1$—$(Y_1)_n$— and $R_2$—$(Y_1)_n$— together are a radical of the formula

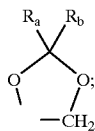

$R_3$ is a direct bond or linear or branched $C_1$–$C_8$alkylene that is unsubstituted or substituted by —OH and/or optionally interrupted by one or more groups —O—, —O—C(O)— or —O—C(O)—O—;

$R_4$ is branched $C_3$–$C_{18}$alkylene, unsubstituted or $C_1$–$C_4$alkyl- or $C_1$–$C_4$alkoxy-substituted $C_6$–$C_{10}$arylene, or unsubstituted or $C_1$–$C_4$alkyl- or $C_1$–$C_4$alkoxy-substituted $C_7$–$C_{18}$-aralkylene, unsubstituted or $C_1$–$C_4$alkyl- or $C_1$–$C_4$alkoxy-substituted $C_3$–$C_8$cycloalkylene, unsubstituted or $C_1$–$C_4$alkyl- or $C_1$–$C_4$alkoxy-substituted $C_3$–$C_8$cycloalkylene-$C_yH_{2y}$- or unsubstituted or $C_1$–$C_4$alkyl- or $C_1$–$C_4$alkoxy-substituted —$C_yH_{2y}$-($C_3$–$C_8$cycloalkylene)-$C_yH_{2y}$—;

$R_5$ independently has the same definitions as $R_4$ or is linear $C_3$–$C_{18}$alkylene;

$R_{1A}$ is lower alkyl;

x is an integer from 3 to 5;

y is an integer from 1 to 6;

$R_a$ and $R_b$ are each independently of the other H, $C_1$–$C_8$alkyl, $C_3$–$C_8$cycloalkyl, benzyl or phenyl;

with the provisos that n in the groups —$(Y_1)_n$—$R_1$ is 0 when $R_2$ is H; that not more than two $Y_1$ of the —$(Y_1)_n$— groups are O and n in the other —$(Y_1)_n$— groups is 0; and that n in the group —$(Y_2)_n$— is 0 when $R_3$ is a direct bond;

and wherein also

X is bivalent —O—, —NH—, —S—, lower alkylene or

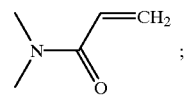

$Y_{10}$ is a direct bond or —O—$(CH_2)_y$— wherein y is an integer from 1 to 6 and the terminal $CH_2$ group of which is linked to the adjacent X in formula (Ib);

$R_{100}$ is H, $C_1$–$C_{12}$alkyl, $C_1$–$C_{12}$alkoxy, $C_1$–$C_{12}$alkylNH— or —$NR_{1A}R_{1B}$ wherein $R_{1A}$ is lower alkyl and $R_{1B}$ is H or lower alkyl;

$R_{101}$ is linear or branched lower alkyl, lower alkenyl or aryl-lower alkyl;

$R_{102}$ independently of $R_{101}$ has the same definitions as $R_{101}$ or is aryl, or $R_{101}$ and $R_{102}$ together are —$(CH_2)_m$— wherein m is an integer from 2 to 6;

$R_{103}$ and $R_{104}$ are each independently of the other linear or branched lower alkyl that may be substituted by $C_1$–$C_4$alkoxy, or aryl-lower alkyl or lower alkenyl; or $R_{103}$ and $R_{104}$ together are —$(CH_2)_z$—$Y_{11}$—$(CH_2)_z$— wherein $Y_{11}$ is a direct bond, —O—, —S— or —$NR_{1B}$—, and $R_{1B}$ is H or lower alkyl and each z independently of the other is an integer from 2 to 4.

In a preferred embodiment, Y is O.

$R_{1A}$ as alkyl may be, for example, methyl, ethyl, n- or iso-propyl, n-, iso- or tert-butyl, pentyl or hexyl. $R_{1A}$ is preferably methyl.

The group R contains as alkyl, alkoxy or alkylNH— preferably from 1 to 6 and especially from 1 to 4 carbon atoms. Some examples are methyl, ethyl, n- or iso-propyl, n-, iso- or tert-butyl, pentyl, hexyl, octyl, decyl, dodecyl, methoxy, ethoxy, propoxy, butoxy and methylNH—. Most preferably, R is H.

$R_1$ as alkyl is preferably linear and contains preferably from 1 to 4 carbon atoms. Some examples are methyl, ethyl, n- or iso-propyl, n-, iso- or tert-butyl, pentyl, hexyl, heptyl and octyl. $R_1$ is especially methyl or ethyl. $R_1$ as aryl may be, for example, naphthyl or especially phenyl. When the two groups $R_1$—$(Y_1)_n$— together are —$(CH_2)_x$—, x is preferably 4 and especially 5. $R_1$ as hydroxyalkyl is preferably linear and contains preferably from 1 to 4 carbon atoms. Some examples are hydroxymethyl and 2-hydroxyeth-1-yl.

For $R_2$ the same preferred definitions as for $R_1$ apply. $R_2$ is preferably H, methyl or ethyl.

$R_a$ and $R_b$ are preferably each independently of the other H or $C_1$–$C_4$alkyl, for example methyl or ethyl.

In a preferred sub-group, $R_1$ is preferably ethyl and especially methyl, or the two groups $R_1$—$(Y_1)_n$— together are pentamethylene, n in the group —$(Y_1)$—$R_2$ is preferably 0, $R_2$ is preferably methyl, hydroxymethyl or H and R is H.

In another preferred embodiment, in the group —$(Y_1)_n$—$R_2$, $Y_1$ is O, n is 1 and $R_2$ is H. In this case, n in the groups $R_1$—$(Y_1)_n$— is especially 0.

$R_3$ contains as alkylene preferably from 1 to 6 and especially from 1 to 4 carbon atoms and the alkylene is preferably linear. Some examples are methylene, ethylene, 1,2- or 1,3-propylene, 1,2-, 1,3- or 1,4-butylene, pentylene, hexylene, heptylene and octylene. Methylene, ethylene, 1,3-propylene and 1,4-butylene are preferred. Most especially, $R_3$ is ethylene; or a direct bond, in which case n in the group —$(Y_2)_n$— is 0.

When $R_3$ is hydroxy-substituted alkylene it may be, for example, especially 2-hydroxy-1,3-propylene or also 2-hydroxy-1,3- or -1,4-butylene. Alkylene interrupted by —O— and unsubstituted or substituted by —OH is, for example, —CH$_2$CH$_2$—O—CH$_2$CH$_2$—, —CH$_2$CH$_2$—O—CH$_2$CH$_2$—O—CH$_2$CH$_2$—, —CH$_2$CH$_2$—O—CH$_2$CH$_2$—O—CH$_2$CH$_2$—O—CH$_2$CH$_2$—, [—CH(CH$_3$)CH$_2$—O—CH(CH$_3$)CH$_2$—], —CH(CH$_3$)CH$_2$—O—CH$_2$CH$_2$—, —CH(C$_2$H$_5$)CH$_2$—O—CH$_2$CH$_2$—, [—CH(C$_2$H$_5$)CH$_2$—O—CH(C$_2$H$_5$)CH$_2$—] or —CH$_2$CH$_2$CH$_2$CH$_2$—O—CH$_2$CH$_2$CH$_2$— and —CH$_2$CH(OH)CH$_2$—O—CH$_2$CH$_2$—. Alkylene interrupted by —O—C(O)— or —C(O)—O— is, for example, —CH$_2$CH$_2$—C(O)—O—CH$_2$— or —CH$_2$CH$_2$—O—C(O)—CH$_2$—. Alkylene interrupted by —O—C(O)—O— is, for example, —CH$_2$CH$_2$—O—C(O)—O—CH$_2$CH$_2$— or —CH$_2$CH$_2$—O—C(O)—O—CH$_2$—.

The substituents $C_1$–$C_4$alkyl and $C_1$–$C_4$alkoxy are preferably methyl or ethyl and methoxy or ethoxy.

$R_4$ contains as branched alkylene preferably from 3 to 14 and especially from 4 to 10 carbon atoms. Examples of alkylene are 1,2-propylene, 2-methyl- or 2,2-dimethyl-1,3-propylene, 1,2-, 1,3- and 2,3-butylene, 2-methyl- or 2,3-dimethyl-1,4-butylene, 1,2-, 1,3- or 1,4-pentylene, 2-methyl- or 3-methyl- or 4-methyl- or 2,3-dimethyl- or 2,4-dimethyl- or 3,4-dimethyl- or 2,3,4-trimethyl- or 2,2,3-trimethyl- or 2,2,4-trimethyl- or 2,2,3,3-tetramethyl- or 2,2,3,4-tetramethyl-1,5-pentylene, 1,2-, 1,3-, 1,4- or 1,5-hexylene, 2-methyl- or 3-methyl- or 4-methyl- or 2,2-dimethyl- or 3,3-dimethyl- or 2,3-dimethyl- or 2,4-dimethyl- or 3,4-dimethyl- or 2,2,3-trimethyl- or 2,2,4-trimethyl- or 2,2,5-trimethyl- or 2,3,4-trimethyl- or 2,2,4,5-tetramethyl-1,6-hexylene, 1,2-, 1,3-, 1,4- 1,5 or 1,6-heptylene, 2-methyl- or 3-methyl- or 4-methyl- or 5-methyl- or 2,2-dimethyl- or 3,3-dimethyl- or 2,3-dimethyl- or 2,4-dimethyl- or 3,4-dimethyl- or 2,2,3-trimethyl- or 2,2,4-trimethyl- or 2,2,5-trimethyl- or 2,2,triethyl- or 2,3,4-trimethyl- or 2,4,5-trimethyl- or 2,4,6-trimethyl- or 2,2,4,5-tetramethyl-1,7-heptylene, 1,2-, 1,3-, 1,4- 1,5- 1,6- or 1,7-octylene, 2-methyl- or 3-methyl- or 4-methyl- or 5-methyl- or 6-methyl- or 7-methyl- or 2,2dimethyl- or 3,3-dimethyl- or 2,3-dimethyl- or 2,4-dimethyl- or 3,4-dimethyl- or 2,6-dimethyl- or 2,7-dimethyl- or 2,2,4-trimethyl- or 2,2,5-trimethyl- or 2,2,6-trimethyl- or 2,2,5,6-tetramethyl-1,8-octylene, 1,2-, 1,3-, 1,4- 1,5- 1,6-, 1,7- or 1,8-nonylene, 2-methyl- or 3-methyl- or 4-methyl- or 5-methyl- or 6-methyl- or 7-methyl- or 8-methyl- or 2,2-dimethyl- or 3,3-dimethyl- or 2,3-dimethyl- or 2,4-dimethyl- or 3,4-methyl- or 2,6-dimethyl- or 2,7-dimethyl- or 2,8-dimethyl- or 2,2,4-trimethyl- or 2,2,5-trimethyl- or 2,2,6-trimethyl- or 2,2,7-trimethyl- or 2,2,8-trimethyl-nonylene, 1,2-, 1,3-, 1,4- 1,5- 1,6-, 1,7-, 1,8- or 1,9-decylene, 2-methyl- or 3-methyl- or 4-methyl- or 5-methyl- or 6-methyl- or 7-methyl- or 8-methyl- or 9-methyl- or 2,2-dimethyl- or 3,3-dimethyl- or 2,3-dimethyl- or 2,4-dimethyl- or 3,4-dimethyl- or 2,6-dimethyl- or 2,7-dimethyl- or 2,8-dimethyl- or 2,9-dimethyl-1,10-decylene, 1,2-, 1,3-, 1,4- 1,5- 1,6-, 1,7-, 1,8-, 1,9- or 1,10-undecylene, 2-methyl- or 3-methyl- or 4-methyl- or 5-methyl- or 6-methyl- or 7-methyl- or 8-methyl- or 9-methyl- or 10-methyl-1,11-undecylene, 1,4- 1,5- 1,6-, 1,7-, 1,8-, 1,9-, 1,10- or 1,11-dodecylene.

Some preferred branched alkylene radicals are 2,2-dimethyl-1,4-butylene, 2,2-dimethyl-1,5-pentylene, 2,2,3- or 2,2,4-trimethyl-1,5-pentylene, 2,2-dimethyl-1,6-hexylene, 2,2,3- or 2,2,4- or 2,2,5-trimethyl-1,6-hexylene, 2,2-dimethyl-1,7-heptylene, 2,2,3- or 2,2,4- or 2,2,5- or 2,2,6-trimethyl-1,7-heptylene, 2,2-dimethyl-1,8-octylene, 2,2,3- or 2,2,4- or 2,2,5- or 2,2,6- or 2,2,7-trimethyl-1,8-octylene.

When $R_4$ is arylene, it is preferably naphthylene and especially phenylene. When the arylene is substituted, one substituent is preferably in the ortho-position with respect to an isocyanate group. Examples of substituted arylene are 1-methyl-2,4-phenylene, 1,5-dimethyl-2,4-phenylene, 1-methoxy-2,4-phenylene and 1-methyl-2,7-naphthylene.

$R_4$ as aralkylene is preferably naphthylalkylene and especially phenylalkylene. The alkylene group in the aralkylene contains preferably from 1 to 12, more preferably from 1 to 6 and especially from 1 to 4 carbon atoms. Most preferably, the alkylene group in the aralkylene is methylene or ethylene. Some examples are 1,3- or 1,4-benzylene, naphth-2-yl-7-methylene, 6-methyl-1,3- or -1,4-benzylene, 6-methoxy-1,3- or -1,4-benzylene.

When $R_4$ is cycloalkylene, it is preferably $C_5$- or $C_6$-cycloalkylene that is unsubstituted or substituted by methyl. Some examples are 1,3-cyclobutylene, 1,3-cyclopentylene, 1,3- or 1,4-cyclohexylene, 1,3- or 1,4-cycloheptylene, 1,3- or 1,4- or 1,5-cyclooctylene, 4-methyl-1,3-cyclopentylene, 4-methyl-1,3-cyclohexylene, 4,4-dimethyl-1,3-cyclohexylene, 3-methyl- or 3,3-dimethyl-1,4-cyclohexylene, 3,5-dimethyl-1,3-cyclohexylene, 2,4-dimethyl-1,4-cyclohexylene.

When $R_4$ is cycloalkylene-$C_yH_{2y}$—, it is preferably cyclopentylene-$C_yH_{2y}$— and especially cyclohexylene-$C_yH_{2y}$— that is unsubstituted or substituted by preferably from 1 to 3 $C_1$–$C_4$alkyl groups, especially methyl groups. In the group —$C_yH_{2y}$—, y is preferably an integer from 1 to 4. More preferably, the group —$C_yH_{2y}$— is ethylene and especially methylene. Some examples are cyclopent-1-yl-3-methylene, 3-methyl-cyclopent-1-yl-3-methylene, 3,4-dimethyl-cyclopent-1-yl-3-methylene, 3,4,4-trimethyl-cyclopent-1-yl-3-methylene, cyclohex-1-yl-3- or 4-methylene, 3- or 4- or 5-methyl-cyclohex-1-yl-3- or -4-methylene, 3,4- or 3,5-dimethyl-cyclohex-1-yl-3- or -4-methylene, 3,4,5- or 3,4,4- or 3,5,5-trimethyl-cyclohex-1-yl-3- or -4-methylene.

When $R_4$ is —$C_yH_{2y}$-cycloalkylene-$C_yH_{2y}$—, it is preferably —$C_yH_{2y}$-cyclopentylene-$C_yH_{2y}$— and especially —$C_yH_{2y}$-cyclohexylene-$C_yH_{2y}$— that is unsubstituted or substituted by preferably from 1 to 3 $C_1$–$C_4$alkyl groups, especially methyl groups. In the group —$C_yH_{2y}$—, y is preferably an integer from 1 to 4. More preferably, the groups —$C_yH_{2y}$— are ethylene and especially methylene. Some examples are cyclopentane-1,3-dimethylene, 3-methyl-cyclopentane-1,3-dimethylene, 3,4-dimethyl-cyclopentane-1,3-dimethylene, 3,4,4-trimethyl-cyclopentane-1,3-dimethylene, cyclohexane-1,3- or -1,4-dimethylene, 3- or 4- or 5-methyl-cyclohexane-1,3- or -1,4-dimethylene, 3,4- or 3,5-dimethyl-cyclohexane-1,3- or -1,4-dimethylene, or 3,4,5- or 3,4,4- or 3,5,5-trimethyl-cyclohexane-1,3- or -1,4-dimethylene.

When $R_5$ has the same definitions as $R_4$, the preferred definitions given hereinbefore for $R_4$ also apply. $R_5$ contains as linear allylene preferably from 3 to 12 and especially from 3 to 8 carbon atoms. Some examples of linear alkylene are 1,3-propylene, 1,4-butylene, 1,5-pentylene, 1,6-hexylene, 1,7-heptylene, 1,8-octylene, 1,9-nonylene, 1,10-decylene, 1,11-undecylene, 1,12-dodecylene, 1,14-tetradecylene and 1,18-octadecylene.

A preferred definition of X is —O—, —NH—, —S— or lower alkylene. More preferably, X is —O— or —S— and especially —O—.

In a preferred definition of $Y_{10}$, the index y is 1 to 5, more preferably 2 to 4, and most preferably 2 or 3, so that $Y_{10}$ is, for example, ethyleneoxy or propyleneoxy. In another preferred definition, $Y_{10}$ is a direct bond, X then preferably being or containing at least one hetero atom.

The group $R_{100}$ contains as alkyl, alkoxy, alkylNH— or —$NR_{1A}R_{1B}$ preferably from 1 to 6 and especially from 1 to 4 carbon atoms. Some examples are methyl, ethyl, n- or isopropyl, n-, iso- or tert-butyl, pentyl, hexyl, octyl, decyl, dodecyl, methoxy, ethoxy, propoxy, butoxy, N,N-dimethylamino and N-methylamino. Most preferably, R is H. A preferred definition of —$NR_{1A}R_{1B}$ is N,N-dimethylamino, N-methylamino, N-methyl-N-ethylamino, N-ethylamino, N,N-diethylamino, N-isopropylamino or N,N-diisopropyl-amino.

$R_{101}$ is preferably allyl, benzyl or linear $C_1$–$C_4$alkyl, for example methyl or ethyl.

$R_{102}$ has preferably the same definitions as $R_{101}$ and is more preferably linear lower alkyl having from 1 to 4 carbon atoms and especially 1 or 2 carbon atoms. $R_{102}$ as aryl may be, for example, naphthyl or especially phenyl that is unsubstituted or substituted by lower alkyl or lower alkoxy. When $R_{101}$ and $R_{102}$ together are —$(CH_2)_m$—, m is preferably 4 or 5 and especially 5.

$R_{103}$ is preferably linear lower alkyl having from 1 to 4 carbon atoms, benzyl or allyl, and more preferably methyl or ethyl.

$R_{104}$ is preferably linear lower alkyl having from 1 to 4 carbon atoms and more preferably methyl or ethyl.

When $R_{103}$ and $R_{104}$ together are —$(CH_2)_z$—$Y_{11}$—$(CH_2)_z$—, $Y_{11}$ is preferably a direct bond, —O— or —$N(CH_3)$— and most preferably —O—; z is preferably 2 or 3 and especially 2.

A preferred sub-group of compounds of formula Ia comprises those wherein, in the groups $R_1$—$(Y_1)_n$—, n is 0, Y, $Y_2$ and $Y_1$ in the group $R_2$—$(Y_1)_n$— are each O, n in the group $R_2$—$(Y_1)_n$— is 0 or 1, $R_1$ is $C_1$–$C_4$alkyl or phenyl or the groups $R_1$—$(Y_1)_n$— together are tetramethylene or pentamethylene, $R_2$ is $C_1$–$C_4$alkyl or H, R is hydrogen, n in the group —$(Y_2)$—$_n$ is 0 or 1 and $R_3$ is linear or branched $C_2$–$C_4$alkylene, or is a direct bond, in which case n in the group —$(Y_2)$—$_n$ is 0, $R_4$ is branched $C_5$–$C_{10}$alkylene, phenylene or phenylene substituted by from 1 to 3 methyl groups, benzylene or benzylene substituted by from 1 to 3 methyl groups, cyclohexylene or cyclohexylene substituted by from 1 to 3 methyl groups, cyclohexyl-$C_yH_{2y}$— or —$C_yH_{2y}$-cyclohexyl-$C_yH_{2y}$— or cyclohexyl-$C_yH_{2y}$— or —$C_yH_{2y}$-cyclohexyl-$C_yH_{2y}$— substituted by from 1 to 3 methyl groups, $R_5$ has the same definitions as $R_4$ or is linear $C_3$–$C_{10}$alkylene, and y is 1 or 2.

An especially preferred sub-group of compounds of formula Ia comprises those wherein, in the groups $R_1$—$(Y_1)_n$— and —$(Y_2)$—$_n$, n is 0, Y, $Y_2$ and $Y_1$ in the group $R_2$—$(Y_1)_n$— are each O, n in the group $R_2$—$(Y_1)_n$— is 0 or 1, $R_1$ is methyl or phenyl or the groups $R_1(Y_1)_n$— together are pentamethylene, $R_2$ is methyl or H, R is hydrogen, n in the group —$(Y_2)$—$_n$ is 1 and $R_3$ is ethylene or n in the group —$(Y_2)$—$_n$ is 0 and $R_3$ is a direct bond, $R_4$ is branched $C_6$–$C_{10}$alkylene, phenylene or phenylene substituted by from 1 to 3 methyl groups, benzylene or benzylene substituted by from 1 to 3 methyl groups, cyclohexylene or cyclohexylene substituted by from 1 to 3 methyl groups, cyclohexyl-$CH_2$— or cyclohexyl-$CH_2$— substituted by from 1 to 3 methyl groups, $R_5$ has the same definitions as $R_4$ or is linear $C_5$–$C_{10}$alkylene.

A preferred sub-group of compounds of formula Ib comprises those wherein $R_{101}$ is linear lower alkyl, lower alkenyl or aryl-lower alkyl;

$R_{102}$ independently of $R_{101}$ has the same definitions as $R_{101}$ or is aryl;

$R_{103}$ and $R_{104}$ are each independently of the other linear or branched lower alkyl that may be substituted by $C_1$–$C_4$alkoxy, or aryl-lower alkyl or lower alkenyl; or $R_{103}$ and $R_{104}$ together are —$(CH_2)_z$—$Y_{11}$—$(CH_2)_z$— wherein $Y_{11}$ is a direct bond, —O—, —S— or —$NR_{1B}$—, and $R_{1B}$ is H or lower alkyl and each z independently of the other is an integer from 2 to 4; and $R_5$ is linear or branched $C_3$–$C_{18}$alkylene, unsubstituted or $C_1$–$C_4$alkyl- or $C_1$–$C_4$alkoxy-substituted $C_6$–$C_{10}$arylene, or unsubstituted or $C_1$–$C_4$alkyl- or $C_1$–$C_4$alkoxy-substituted $C_7$–$C_{18}$aralkylene, unsubstituted or $C_1$–$C_4$alkyl- or $C_1$–$C_4$alkoxy-substituted $C_{13}$–$C_{24}$-arylenealkylenearylene, unsubstituted or $C_1$–$C_4$alkyl- or $C_1$–$C_4$alkoxy-substituted $C_3$–$C_8$-cycloalkylene, unsubstituted or $C_1$–$C_4$alkyl- or $C_1$–$C_4$alkoxy-substituted $C_3$–$C_8$cycloalkylene-$C_yH_{2y}$- or unsubstituted or $C_1$–$C_4$alkyl- or $C_1$–$C_4$alkoxy-substituted —$C_yH_{2y}$-($C_3$–$C_8$cycloalkylene)-$C_yH_{2y}$— wherein y is an integer from 1 to 6.

A preferred sub-group of compounds of formula Ib comprises those wherein

X is bivalent —O—, —NH—, —S— or —$(CH_2)_y$—;

$Y_{10}$ is a direct bond or —O—$(CH_2)_y$— wherein y is an integer from 1 to 6 and the terminal $CH_2$ group of which is linked to the adjacent X in formula (Ib);

$R_{100}$ is H, $C_1$–$C_{12}$alkyl or $C_1$–$C_{12}$alkoxy;

$R_{101}$ is linear lower alkyl, lower alkenyl or aryl-lower alkyl;

$R_{102}$ independently of $R_{101}$ has the same definitions as $R_{101}$ or is aryl, or $R_{101}$ and $R_{102}$ together are —$(CH_2)_m$— wherein m is an integer from 2 to 6;

$R_{103}$ and $R_{104}$ are each independently of the other linear or branched lower alkyl that may be substituted by $C_1$–$C_4$alkoxy, or aryl-lower alkyl or lower alkenyl; or $R_{103}$ and $R_{104}$ together are —$(CH_2)_z$—$Y_{11}$—$(CH_2)_z$— wherein $Y_{11}$ is a direct bond, —O—, —S— or —$NR_{1B}$—, and $R_{1B}$ is H or lower alkyl and each z independently of the other is an integer from 2 to 4; and $R_5$ is branched $C_6$–$C_{10}$alkylene, phenylene or phenylene substituted by from 1 to 3 methyl groups, benzylene or benzylene substituted by from 1 to 3 methyl groups, cyclohexylene or cyclohexylene substituted by from 1 to 3 methyl groups, cyclohexylene-$CH_2$— or cyclohexylene-$CH_2$— substituted by from 1 to 3 methyl groups.

An especially preferred sub-group of compounds of formula Ib comprises those wherein $R_{101}$ is methyl, allyl, toluylmethyl or benzyl, $R_{102}$ is methyl, ethyl, benzyl or phenyl, or $R_{101}$ and $R_{102}$ together are pentamethylene, $R_{103}$ and $R_{104}$ are each independently of the other lower alkyl having up to 4 carbon atoms or $R_{103}$ and $R_{104}$ together are —$CH_2CH_2OCH_2CH_2$—, and $R_5$ is branched $C_6$–$C_{10}$alkylene, phenylene or phenylene substituted by from 1 to 3 methyl groups, benzylene or benzylene substituted by from 1 to 3 methyl groups, cyclohexylene or cyclohexylene substituted by from 1 to 3 methyl groups, cyclohexylene-$CH_2$— or cyclohexylene-$CH_2$— substituted by from 1 to 3 methyl groups.

The groups $R_4$ and $R_5$ are especially groups wherein the reactivity of the OCN group is reduced, this being achieved essentially by steric hindrance or electronic influences at at least one adjacent carbon atom. $R_4$ and $R_5$ are preferably, therefore, alkylene that is branched in the α-position or especially the β-position with respect to the OCN group, or are cyclic hydrocarbon radicals that are substituted as defined in at least one α-position.

Some examples of especially preferred compounds are

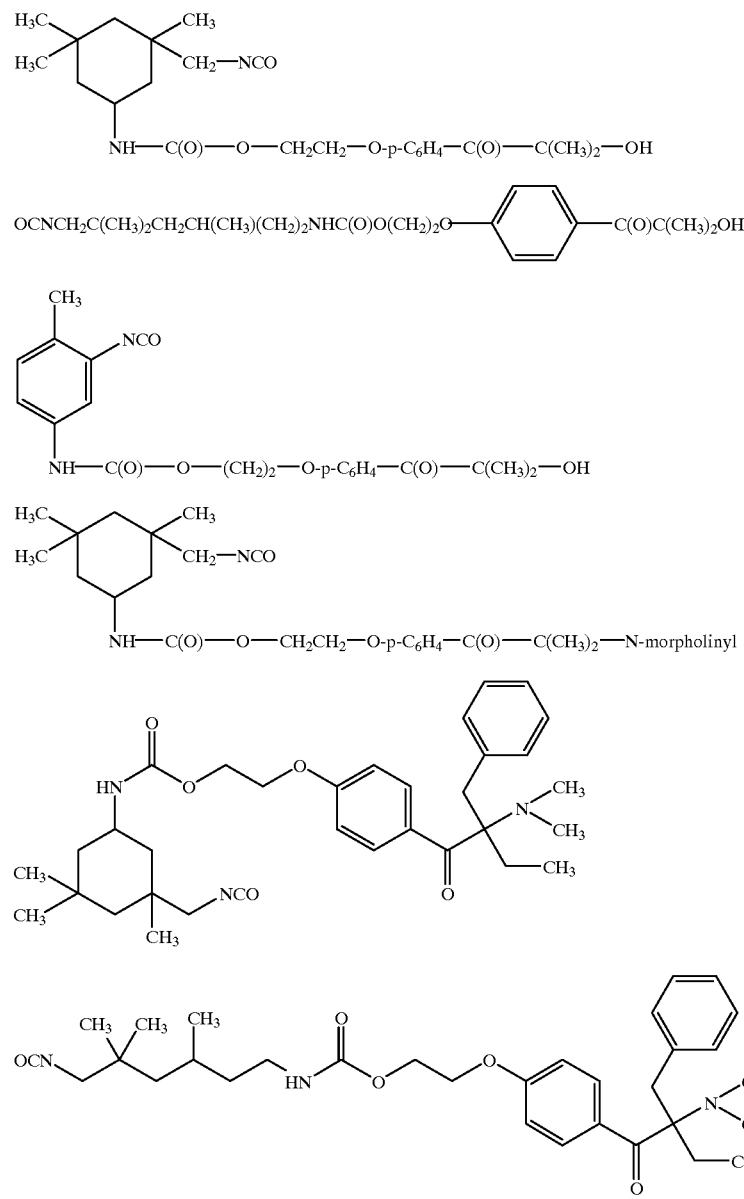

-continued

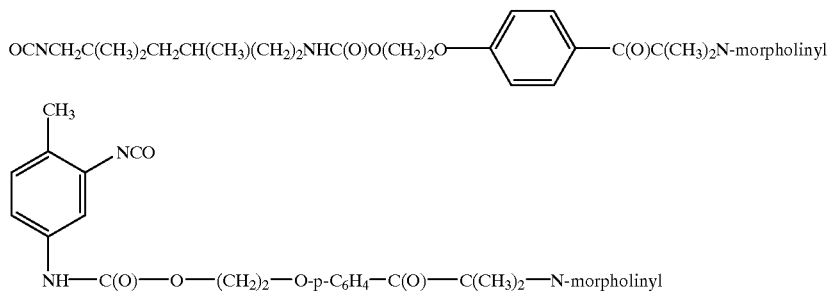

The preparation of a compound of formula Ia or Ib comprises reacting a compound of formula IIa or IIb

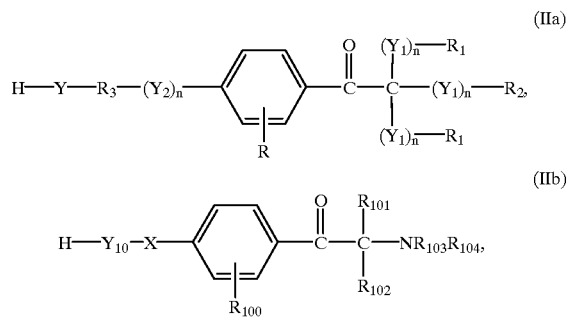

wherein X, Y, $Y_1$, $Y_2$, $Y_{10}$, R, $R_1$, $R_2$, $R_3$, $R_{100}$, $R_{101}$, $R_{102}$, $R_{103}$, $R_{104}$ and n are as defined hereinbefore, preferably in an inert organic solvent, with a diisocyanate of formula IIIa or IIIb or with such a diisocyanate optionally mono-masked, $$OCN—R_4—NCO, \quad (IIIa)$$

$$OCN—R_5—NCO \quad (IIIb)$$

wherein $R_4$ and $R_5$ are as defined hereinbefore.

Preferred examples of diisocyanates wherein the reactivity of the two isocyanato groups is distinctly different are e.g. hexane-1,6-diisocyanate, 2,2,4-trimethylhexane-1,6-diisocyanate, 1,3-bis-(3-isocyanatopropyl)-tetramethyldisiloxane, tetramethylenediisocyanate, phenylene-1,4-diisocyanate, toluene-2,4-diisocyanate, toluene-2,6-diisocyanate, m- or p-xylenediisocyanate, isophoronediisocyanate, cyclohexane-1,4-diisocyanate, 1,5-naphthylenediisocyanate, 4,4'-diphenylmethanediisocyanate, 4,4'-diphenylsulfonediisocyanate or 4,4'-dicyclohexylmethanediisocyanate.

Masking agents are known from urethane chemistry. They may be, for example, phenols (cresol, xylenol), lactams (ε-caprolactam), oximes (acetoxime, benzophenone oxime), H-active methylene compounds (diethyl malonate, ethyl acetoacetate), pyrazoles or benzotriazoles. Masking agents are described, for example, by Z. W. Wicks, Jr. in Progress in Organic Coatings, 9 (1981), pages 3–28.

The starting materials of the type shown in formula IIa or IIb are known and are described, for example, in EP-A-284 561, EP-A-117 233 or EP-A-088 050.

Suitable inert solvents are aprotic, preferably polar, solvents such as, for example, hydrocarbons (petroleum ether, methylcyclohexane, benzene, toluene, xylene), halogenated hydrocarbons (chloroform, methylene chloride, trichloroethane, tetrachloroethane, chlorobenzene), ethers (diethyl ether, dibutyl ether, ethylene glycol dimethyl ether, diethylene glycol dimethyl ether, tetrahydrofuran (THF), dioxane), ketones (acetone, dibutyl ketone, methyl isobutyl ketone), carboxylic acid esters and lactones (ethyl acetate, butyrolactone, valerolactone), alkylated carboxylic acid amides (N,N-dimethylacetamide, N,N-dimethylformamide (DMF) or N-methyl-2-pyrrolidone (NMP)), nitriles (acetonitrile), sulfones and sulfoxides (dimethyl sulfoxide (DMSO), tetramethylenesulfone). Polar solvents are preferably used.

The reactants are advantageously used in equimolar quantities. The reaction temperature may, for example, be from 0 to 200° C. When using catalysts, the temperatures may advantageously be in the range from −20° to 60° C. and preferably in the range from −10° to 50° C. Suitable catalysts are, for example, metal salts, such as alkali metal salts, of carboxylic acids, tertiary amines, for example $(C_1-C_6alkyl)_3N$ (triethylamine, tri-n-butylamine), N-methylpyrrolidine, N-methylmorpholine, N,N-dimethylpiperidine, pyridine and 1,4-diaza-bicyclooctane. Certain tin compounds have been found to be especially effective, especially alkyltin salts of carboxylic acids, such as, for example, dibutyltin dilaurate, or, for example, tin dioctoate.

If free OH or NH groups are present in the compounds of formula Ia or Ib, those groups can initially be protected by suitable protecting groups during the reaction with a diisocyanate and subsequently freed again by removing the protecting groups. Suitable protecting groups are known to the person skilled in the art. Representative examples can be found, for example, in T. W. Greene, "Protective Groups in Organic Synthesis", Wiley Interscience, 1981.

The isolation and purification of the compounds prepared are carried out in accordance with known methods, for example extraction, crystallisation, re-crystallisation or chromatographic purification methods. The compounds are obtained in high yields and purity. The yields in the case of non-optimised processes may be more than 85% of the theoretical yields.

The term "macroinitiator" is used within the scope of the present invention to mean an oligomer or polymer having one or more H-active —OH and/or —NH— groups bonded terminally or pendantly, if desired via one or more bridge groups, the H atoms of which H-active groups are partly or completely substituted by radicals $R_{200}$, wherein $R_{200}$ is a radical of formula IVa or IVb

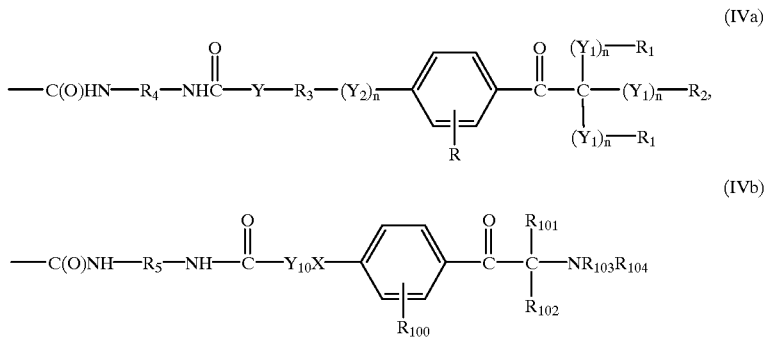

wherein X, Y, $Y_1$, $Y_2$, $Y_{10}$, R, $R_1$, $R_2$, $R_3$, $R_4$, $R_5$, $R_{100}$, $R_{101}$, $R_{102}$, $R_{103}$, $R_{104}$ and n are as defined hereinbefore.

The H-active groups are preferably —COOH, OH— or —NH— groups.

The oligomers may have, for example, an average molecular weight of from 300 to 10000 dalton and contain preferably at least 3, more preferably from 3 to 50 and especially from 5 to 20 structural units. As is known, the transition between oligomers and polymers is fluid and cannot be defined exactly. The polymers may contain from 50 to 10000, more preferably from 50 to 5000, structural units and may have an average molecular weight of from 10000 to 1000000, preferably from 10,000 to 500000. The oligomers and polymers may also comprise up to 95 mol %, preferably from 5 to 90 mol %, comonomeric structural units without H-active groups, based on the polymer.

The oligomers and polymers having H-active groups may be natural or synthetic oligomers or polymers. Examples of these have been mentioned above.

Preferred oligomers and polymers are, for example, cyclodextrins having a total of from 6 to 8 glucose structural units forming a ring, or hydroxyalkyl or aminoalkyl derivatives or derivatives additionally substituted by glucose or maltose radicals, of which at least one structural unit corresponds to formula (V)

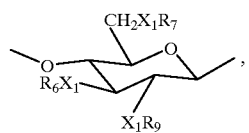

wherein $R_7$, $R_8$ and $R_9$ are each independently of the others H, $C_1$–$C_4$alkyl, especially methyl, $C_2$–$C_6$acyl, especially acetyl, $C_1$–$C_4$hydroxyalkyl, especially hydroxymethyl or 2-hydroxyeth-1-yl, $C_2$–$C_{10}$aminoalkyl and especially $C_2$–$C_4$aminoalkyl, for example 2-aminoeth-1-yl or 3-aminoprop-1-yl or 4aminobut-1-yl, $X_1$ is —O— or —$NR_{1B}$—, wherein, per cyclodextrin unit, a total of from 1 to 10 and preferably from 1 to 6 radicals $X_1$ may be —$NR_{1B}$— and the remaining radicals $X_1$ are —O—, wherein $R_{1B}$ is hydrogen or lower alkyl; and at least one of the radicals $R_7$, $R_8$ and $R_9$ is a radical of formula (VI)

$$—R_{10}—R_{200} \quad (VI)$$

wherein the variables are as defined hereinbefore, and $R_{10}$ is a direct bond, —($C_1$–$C_6$alkylene-O)— or —($C_2$–$C_{10}$alkylene-NH)—.

In a preferred embodiment, from at least half the glucose units to all 6 to 8 of the glucose units contain at least one radical of formula (VI). Also preferred is an embodiment in which only one glucose unit carries a radical of formula (VI). For X, Y, $Y_1$, $Y_2$, $Y_{10}$, R, $R_1$, $R_2$, $R_3$, $R_4$, $R_5$, $R_{100}$, $R_{101}$, $R_{102}$, $R_{103}$, $R_{104}$ and n the preferred definitions given hereinbefore apply. $R_{10}$ is preferably a direct bond —$CH_2$—O—, —$CH_2CH_2$—O—, —$CH_2CH_2$—NH—, —$CH_2CH_2CH_2$—NH— or —$CH_2CH_2CH_2CH_2CH_2$—NH—.

Preferred oligomers or polymers are especially biomolecules, for example hyaluronic acid, dextran or collagen.

Other preferred oligomers and polymers are, for example, oligo- and poly-siloxanes having OH or $NH_2$ groups in alkyl, alkoxyalkyl or aminoalkyl terminal groups or sidechains, the H atoms of which are substituted by a photoinitiator according to the invention. They may also be random, alternating or segmented copolymers or oligomers, for example block copolymers.

More preferred oligomers and polymers are those which comprise a) from 5 to 100 mol % structural units of formula (VII)

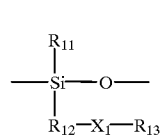

and b) from 95 to 0 mol % structural units of formula (VIII)

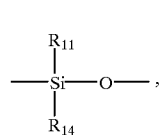

based on the oligomer or polymer, wherein $R_1$, is $C_1$–$C_4$alkyl, lower alkenyl, cyano-lower alkyl or aryl each unsubstituted or partly or completely substituted by F, and is preferably methyl, ethyl, vinyl, allyl, phenyl, cyanopropyl or trifluoromethyl, $R_{12}$ is $C_2$–$C_6$alkylene, preferably 1,3-propylene, or alkylene interrupted once or several times by —O— or —NH—, for example —$(CH_2)_z$—(O—$CH_2$—$CHCH_3$—$)_z$—, or —$(CH_2)_z$—(O—$CH_2$—$CH_2)_z$—, preferably, for example, —$(CH_2)_3$—(O—$CH_2$—$CHCH_3$—$)_2$—, wherein each z idependendy of the other is an integer from 2 to 4, $R_{14}$ has the same definitions as $R_{11}$ or is —$R_{12}$—$X_1$—H or —$R_{12}$—$X_1$—$R_{15}$—H, $X_1$ is —O— or —NH—, and $R_{13}$ is a radical of formula (IX)

—R$_{15}$—R$_{200}$ (IX)

wherein the variables have the definitions given hereinbefore, including their preferred definitions, and R$_{15}$ is a direct bond or a group —C(O)—(CHOH)$_r$—CH$_2$—O— wherein r is 0 or an integer from 1 to 4. X$_1$ is preferably —NH—.

The oligomers or polymers described above contain either one or more pendant radicals of formula IX, or, in addition to one or more pendant radicals of formula IX, also one or two terrninal radicals of formula IX.

Preferred oligomeric and polymeric siloxanes are also those of formula (X)

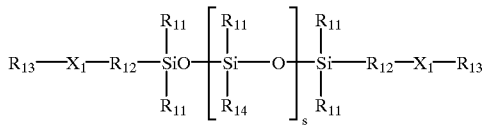

wherein R$_{11}$ is C$_1$–C$_4$alkyl, vinyl, allyl or phenyl each unsubstituted or partly or completely substituted by F, and is preferably methyl, R$_{12}$ is C$_2$–C$_6$alkylene, preferably 1,3-propylene, R$_{14}$ has the same definitions as R$_{11}$ or is —R$_{12}$—X$_1$—H or —R$_{12}$—X$_1$—R$_{15}$—H, X$_1$ is —O— or —NH—, s is an integer from 0 to 1000 and preferably from 0 to 100, and R$_{13}$ is a radical of the above formula (IX) wherein the variables have the definitions given hereinbefore, including the preferred definitions, and R$_{15}$ is a direct bond or a group —C(O)—(CHOH)$_r$—CH$_2$—O— wherein r is 0 or an integer from 1 to 4. X$_1$ is preferably —NH—.

Other preferred oligomers and polymers are those based on oligovinyl and polyvinyl alcohol in which the H atoms in the OH groups are partly or completely substituted by a radical of formula (VI). They may be homopolymers with —CH$_2$CH(OH)— structural units or copolymers with other monovalent or bivalent structural units of olefins.

More preferred are those oligomers and polymers which comprise a) from 5 to 100 mol % structural units of formula (XI)

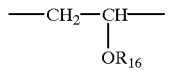

and b) from 95 to 0 mol % structural units of formula (XII)

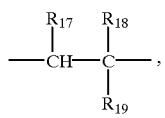

wherein R$_{16}$ is a radical of the above formula (VI) wherein the variables have the definitions given hereinbefore, including the preferred definitions, and R$_{10}$ is a direct bond, —(C$_1$–C$_4$alkylene-O)— or —(C$_2$–C$_{10}$alkylene-NH)—; R$_{17}$ is H, C$_1$–C$_6$alkyl, —COOR$_{20}$ or —COO$^\ominus$, R$_{18}$ is H, F, Cl, CN or C$_1$–C$_6$alkyl, and R$_{19}$ is H, OH, R$_{10}$—H, F, Cl, CN, R$_{20}$—O—, C$_1$–C$_{12}$alkyl, —COO$^{63}$, —COOR$_{20}$, —OCO—R$_{20}$, methylphenyl or phenyl, wherein R$_{20}$ is C$_1$–C$_{18}$alkyl, C$_5$–C$_7$cycloalkyl, (C$_1$–C$_{12}$alkyl)-C$_5$–C$_7$cycloalkyl, phenyl, (C$_1$–C$_{12}$alkyl)-phenyl, benzyl or (C$_1$–C$_{12}$alkyl)benzyl.

R$_{17}$ is preferably H. When R$_{17}$ is alkyl, it is preferably methyl or ethyl. When R$_{17}$ is —COOR$_{20}$, R$_{20}$ is preferably C$_1$–C$_{12}$alkyl, especially C$_1$–C$_6$alkyl.

When R$_{18}$ is alkyl, it is preferably C$_1$–C$_4$alkyl, e.g. methyl, ethyl, n-propyl or n-butyl. R$_{18}$ is preferably H, Cl or C$_1$–C$_4$alkyl.

When R$_{19}$ is the group R$_{20}$—O—, R$_{20}$ is preferably C$_1$–C$_{12}$alkyl, especially C$_1$–C$_6$alkyl. When R$_{19}$ is alkyl, it preferably contains from 1 to 6, especially from 1 to 4, carbon atoms. When R$_{19}$ is the group —COOR$_{20}$, R$_{20}$ is preferably C$_1$–C$_{12}$alkyl, especially C$_1$–C$_6$alkyl, or cyclopentyl or cyclohexyl. When R$_{19}$ is the group —OCO—R$_{20}$, R$_{20}$ is preferably C$_1$–C$_{12}$alkyl, especially C$_1$–C$_6$alkyl, or phenyl or benzyl.

In a preferred embodiment, R$_{17}$ is H, R$_{18}$ is H, F, Cl, methyl or ethyl, and R$_{19}$ is H, OH, F, Cl, CN, C$_1$–C$_4$alkyl, C$_1$–C$_6$alkoxy, C$_1$–C$_6$hydroxyalkoxy, —COO—C$_1$–C$_6$alkyl, —OOC—C$_1$–C$_6$-alkyl or phenyl.

Especially preferred are those oligomers and polymers wherein R$_{17}$ is H, R$_{18}$ is H or methyl, and R$_{19}$ is H, OH, CN, methyl, OCH$_3$, O(CH$_2$)$_t$OH or —COOCH$_3$, and t is an integer from 2 to 6.

Another preferred group of oligomers and polymers comprises partly or completely hydroxyalkylated oligo- or polyacrylates or -methacrylates, or -acrylamides or -methacrylamides, in which the primary hydroxy group or amino group, respectively, is substituted by a radical of the above formula (IX). They may comprise, for example, from 5 to 100 mol % structural units of formula (XIII)

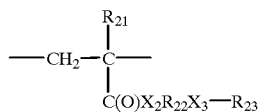

and from 95 to 0 mol % structural units of formula (XIV)

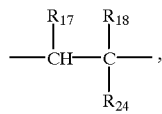

wherein R$_{21}$ is H or methyl, X$_2$ and X$_3$ are each independently of the other —O— or —NH—, R$_{22}$ is —(CH$_2$)$_c$— and c is an integer from 2 to 12, preferably from 2 to 6, R$_{23}$ is a radical of formula (IX), R$_{17}$ and R$_{18}$ are as defined hereinbefore, and R$_{24}$ has the same definitions as R$_{19}$ or is —C(O)X$_2$R$_{22}$X$_3$H. For R$_{23}$, R$_{17}$, R$_{18}$ and R$_{19}$ the preferred definitions mentioned hereinbefore apply. For X$_2$ and X$_3$ the preferred definitions mentioned hereinbefore apply.

Other preferred oligomers and polymers are those consisting of polyalkylene oxides in which the H atoms of the terminal OH or —NH$_2$ groups are partly or completely substituted by radicals of formula (IX). They may, for example, be those of formula (XV) having identical or different structural repeating units —[CH$_2$CH(R$_{26}$)—O]—

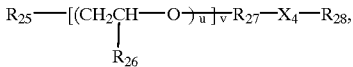

wherein

R$_{25}$ is the group R$_{28}$—X$_4$— or is the v-valent radical of an alcohol or polyol having from 1 to 20 carbon atoms, $R_{26}$ is H, $C_1$–$C_8$alkyl, preferably $C_1$–$C_4$alkyl and especially methyl, $R_{27}$ together with $X_4$ is a direct bond or $R_{27}$ is $C_2$–$C_6$alkylene, preferably $C_3$–$C_6$alkylene and especially 1,3-propylene, $X_4$ is —O— or —NH—, $R_{28}$ is a radical of formula (IX), each u idependently of the other is a numerical value from 3 to 10000, preferably from 5 to 5000, especially from 5 to 1000 and more especially from 5 to 100, and v is an integer from 1 to 6, preferably from 1 to 4.

$R_{25}$ may be a mono- to tetra-valent radical of an alcohol or polyol. When $R_{25}$ is the radical of an alcohol, $R_{25}$ is preferably linear or branched $C_3$–$C_{20}$-alkyl or -alkenyl, $C_3$–$C_8$- and especially $C_5$–$C_6$-cycloalkyl, —$CH_2$-($C_5$–$C_6$cycloalkyl), $C_6$–$C_{10}$aryl and especially phenyl and naphthyl, $C_7$–$C_{16}$aralkyl and especially benzyl and 1-phenyleth-2-yl. The cyclic or aromatic radicals may be substituted by $C_1$–$C_{18}$alkyl or $C_1$–$C_{18}$alkoxy.

When $R_{25}$ is the radical of a diol, $R_{25}$ is preferably branched and especially linear $C_3$–$C_{20}$-alkylene or alkenylene and more preferably $C_3$–$C_{12}$alkylene, $C_3$–$C_8$- and especially $C_5$–$C_6$ -cycloalkylene, —$CH_2$-($C_5$–$C_6$cycloalkyl)—, —$CH_2$-($C_5$–$C_6$cycloalkyl)-$CH_2$—, $C_7$–$C_{16}$aralkylene and especially benzylene, —$CH_2$-($C_6$–$C_{10}$aryl)-$CH_2$— and especially xylylene. The cyclic or aromatic radicals may be substituted by $C_1$–$C_{12}$alkyl or $C_1$–$C_{12}$alkoxy.

When $R_{25}$ is a trivalent radical, it is derived from aliphatic or aromatic tiols. $R_{25}$ is preferably a trivalent aliphatic radical having from 3 to 12 carbon atoms that is derived especially from triols having preferably primary hydroxy groups. Most preferably, $R_{25}$ is —$CH_2$(CH—)$CH_2$—, HC($CH_2$—)$_3$ or $CH_3$C($CH_2$—)$_3$.

When $R_{25}$ is a tetravalent radical, it is derived preferably from aliphatic tetrols. $R_{25}$ is in that case preferably C($CH_2$—)$_4$.

Preferably, $R_{25}$ is a radical derived from Jeffamins (Texaco), a Pluriol, a Poloxamer (BASF) or poly(tetramethylene oxide).

For $R_{28}$ the preferred definitions mentioned hereinbefore apply. Especially preferred are homo-oligomers and homopolymers and block oligomers and block polymers each having structural units of the formula —[$CH_2CH_2$—O]— or —[$CH_2CH(CH_3)$—O]—.

Also suitable are fluorinated polyethers corresponding to formula (XVI)

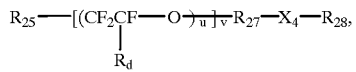

(XVI)

wherein $R_{27}$, $R_{28}$, $X_4$, u and v are as defined hereinbefore, $R_{25}$ is as defined hereinbefore or is the monovalent radical of a partially fluorinated or per-fluorinated alcohol having from 1 to 20, preferably from 1 to 12 and especially from 1 to 6 carbon atoms, or the bivalent radical of a partially fluorinated or per-fluorinated diol having from 2 to 6, preferably from 2 to 4 and especially 2 or 3 carbon atoms, and $R_d$ is F or perfluoroalkyl having from 1 to 12, preferably from 1 to 6 and especially from 1 to 4 carbon atoms.

$R_d$ is especially —$CF_3$.

Other suitable oligomers and polymers are, for example, polyamines, such as polyvinylamine, or polyethyleneimines, in which the H atoms of the NH groups are substituted by a radical of formula (VI), including the preferences already mentioned. Also suitable is poly-ε-lysine.

The oligomers and polymers according to the invention can be prepared simply and in a manner known per se by reaction of a compound of formula Ia or Ib with HO- or NH-functional oligomers and polymers.

Within the scope of the present invention, hereinbefore and hereinafter and unless stated otherwise, arylene is preferably phenylene or napthylene each unsubstituted or substituted by lower alkyl or lower alkoxy, especially 1,3-phenylene, 1,4-phenylene or methyl-1,4-phenylene, or 1,5-naphthylene or 1,8-naphthylene.

Within the scope of the present invention, aryl has up to 24, and preferably up to 18, carbon atoms and is a carbocyclic aromatic compound that is unsubstituted or substituted by lower alkyl or lower alkoxy. Examples are phenyl, toluyl, xylyl, methoxyphenyl, tertbutoxyphenyl, naphthyl or phenanthryl.

Within the scope of this invention, unless defined otherwise the term "lower" used in connection with radicals and compounds denotes especially radicals or compounds having up to 8 carbon atoms, preferably up to 6 carbon atoms.

Lower alkyl has especially up to 8 carbon atoms, preferably up to 6 carbon atoms, and is, for example, methyl, ethyl, propyl, butyl, tert-butyl, pentyl, hexyl or isohexyl.

Lower alkenyl is linear or branched alkenyl having from 2 to 8 carbon atoms, preferably from 2 to 6 carbon atoms and especially from 2 to 4 carbon atoms. Examples of alkenyl are vinyl, allyl, 1-propen-2-yl, 1-buten-2- or -3- or 4-yl, 2-buten-3-yl, and the isomers of pentenyl, hexenyl or octenyl.

Unless defined otherwise, alkylene has up to 10 carbon atoms and may be straight-chain or branched. Suitable examples include decylene, octylene, hexylene, pentylene, butylene, propylene, ethylene, methylene, 2-propylene, 2-butylene or 3-pentylene. Alkylene is preferably lower alkylene.

Lower alkylene is alkylene having up to 8, and especially up to 6, carbon atoms. An especially preferred definition of lower alkylene is methylene or ethylene.

The arylene unit of alkylenearylene or arylenealkylene is preferably phenylene that is unsubstituted or substituted by lower alkyl or lower alkoxy; the alkylene unit thereof is preferably lower alkylene, such as methylene or ethylene, especially methylene. Preferably, such radicals are therefore phenylenemethylene or methylenephenylene.

Lower alkoxy has especially up to 8 carbon atoms, preferably up to 6 carbon atoms, and is, for example, methoxy, ethoxy, propoxy, butoxy, tert-butoxy or hexyloxy.

Within the scope of the present invention, aryl-lower alkyl has up to 30, preferably up to 24, and especially up to 18, carbon atoms and is lower alkyl substituted by aryl. Examples of aryl-lower alkyl are benzyl, xylylmethyl, toluylethyl, phenylbutyl, tert-butoxyphenylmethyl, naphthylpropyl, methoxyphenylmethyl or phenylhexyl.

The photochemical stimulation of a photoinitiator or the polymerisation is carried out in accordance with known methods, for example by irradiation with light that is high in short-wave radiation and is preferably UV light. Suitable light sources are, for example, mercury medium-pressure, high-pressure and low-pressure radiators, super-actinic fluorescent tubes, metal halide lamps or lasers, the emission maxima of which lie in the range from 250 to 450 nm. In the case of a combination with photo-sensitizers or ferrocene derivatives, it is also possible to use longer-wavelength light or laser beams up to 600 nm.

In certain cases, it may be advantageous to use mixtures of two or more of the abovementioned photoinitiators. Mixtures with customary commercial photoinitiators can, of course, also be used, for example mixtures with benzophenone, acetophenone derivatives, bezoin ethers or benzil ketals.

To accelerate a photo-chemical step amines may be added, e.g. triethanolamine, N-methyl-diethanolamine, p-dimethylaminobenzoic acid ethyl ester or Michler's ketone. The action of the amines can be intensified by the addition of aromatic ketones of the benzophenone type. Acceleration can also be brought about by the addition of photosensitizers, which shift or broaden the spectral sensitivity. These are especially aromatic carbonyl compounds, for example derivatives of benzophenone, thioxanthone, anthraquinone and 3-acylcoumarin, and 3-(aroylmethylene)-thiazolines. If desired, the photochemical reaction stage can be specifically sensitized to certain wavelength ranges of the light and in that way, when various photoinitiators are being used, the reaction sequence can be controlled in a specific manner.

The effectiveness of a photoinitiator used can be increased by the addition of titanocene derivatives having fluoro-organic radicals, as are described in EP-A-122 223 and EP-A-186 626, for example in an amount of from 1 to 20%. Examples of such titanocenes are bis(methylcyclopentadienyl)-bis(2,3,6-trifluorophenyl)-titanium, bis(cyclopentadienyl)-bis(4-dibutylamino-2,3,5,6-tetrafluorophenyl)-titanium, bis(methylcyclopentadienyl)-2-(trifluoromethyl)phenyl-titanium isocyanate, bis(cyclopentadienyl)-2-(trifluoromethyl)phenyl-titanium trifluoroacetate or bis(methylcyclopentadienyl)-bis(4-decyloxy-2,3,5,6tetrafluorophenyl)-titanium. Liquid α-aminoketones are especially suitable for these mixtures.

In the process for coating a surface, in addition to a photoinitiator, various additives may be used, usually in small amounts. Examples of the latter are thermal inhibitors, which are intended, for example, to prevent premature polymerisation, such as, for example, hydroquinone or sterically hindered phenols. In order to increase the dark storage stability, it is possible to use, for example, copper compounds, phosphorus compounds, quaternary ammonium compounds or hydroxylamine derivatives. For the purpose of excluding atmospheric oxygen during the copolymerisation paraffin or similar waxy substances may be added which migrate to the surface when polymerisation commences. As light-protecting agents it is possible to add, in small quantities, UV absorbers, for example those of the benzotriazole, benzophenone or oxalanilide type. Better still is the addition of light-protecting agents that do not absorb UV light, such as, for example, sterically hindered amines (HALS).

The Examples given below serve to illustrate the present invention in more detail; they are not, however, intended to limit the scope thereof in any way. Unless stated otherwise, temperatures are given in degrees Celsius.

PREPARATION EXAMPLES

Example A1
2-Dimethylamino-2-benzyl-1-(4-(2-hydroxyethoxy) phenyl)-butan-1-one.

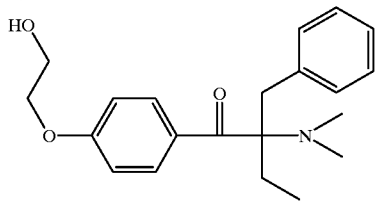

The title compound is prepared in accordance with the synthesis described in EP-A-284 561.

Example A2
2-Ethyl-2-methylamino-1-(4-(2-hydroxyethoxy)phenyl)-pent-4-en-1-one.

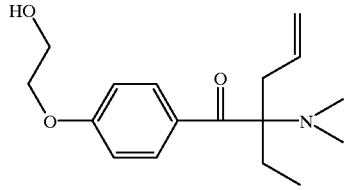

The title compound is prepared in quantitative yield analogously to Example A1. Yellowish crystals of m.p. 80–82° C. remain.

Example A3
2-Ethyl-2-dimethylamino-1-(4-(2-hydroxyethoxy)phenyl)-pentan-1-one.

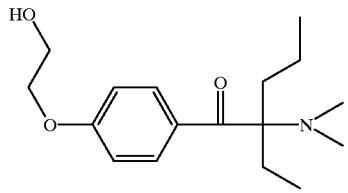

32.6 g (0.11 mol) of 2-ethyl-2-dimethylamino-1-(4-(2-hydroxyethoxy)phenyl)-pent-4-en-1-one according to Example A2 are dissolved in 220 ml of ethyl acetate, 1.6 g of palladium-on-carbon (5%) are added thereto and the mixture is then hydrogenated at 30° C. under normal pressure. After approximately 3 hours the absorption of hydrogen ceases (2.58 liters, 103% of the theoretical amount). The catalyst is removed by filtration and the solvent is distilled off using a rotary evaporator (RE). The oily residue is purified by flash-chromatography (petroleum ether/ethyl acetate 2:1). 27.4 g (84%) of a slightly yellowish oil remain.

Example A4
1-(4-(2-Hydroxyethylthio)phenyl)-2-methyl-2-morpholino-propan-1-one.

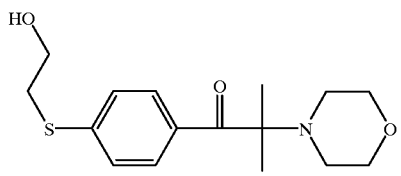

The preparation of the title compound is described in EP-A-088 050.

Example A5
1-(4-(2-Hydroxyethoxy)phenyl)-2-methyl-2-morpholino-propan-1-one.

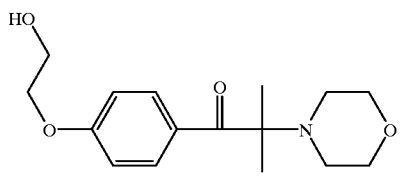

The title compound is prepared analogously to Example A4.

Example A6

Preparation of the following compound:

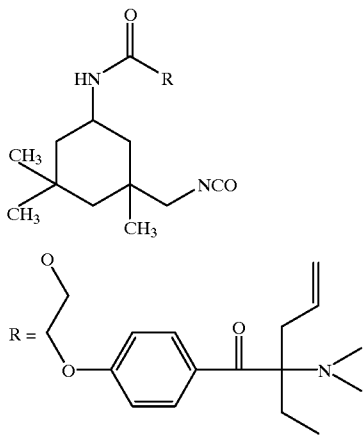

In a 100 ml flask equipped with reflux condenser, thermometer, stirrer and nitrogen inlet pipe, 2.92 g (10 mmol) of 2-ethyl-2-dimethylamino-1-(4-(2-hydroxyethoxy)phenyl)-pent-4-en-1-one (from Example A2) are dissolved in 30 ml of dry methylene chloride, and the solution is mixed with 2.22 g (10 mmol) of IPDI dissolved in 30 ml of dry methylene chloride. 2.0 mg of the catalyst DBTDL are added thereto and stirrng is carried out at RT for 72 hours. The course of the reaction is monitored by TLC (eluant is toluene/acetone 6:1). The reaction solution is then stirred into water. The organic phase is separated off and washed twice more with water. The organic phase is dried over $MgSO_4$ and concentrated using a RE. The residue which remains is purified by column chromatography (toluene/acetone 6:1). 3.4 g (66%) of a yellow oil remain. The structure is verified by proton NMR, IR and elemental analysis.

Example A7

Analogously to Example A6, the following isocyanate is prepared from 1.17 g (4 mmol) of 1-(4-(2-hydroxyethoxy)phenyl)-2-methyl-2-morpholino-propan-1-one (from Example A5) and 0.7 g (4 mmol) of 2,4-TDI using DBTDL as catalyst in methylene chloride. After the addition of 50 ml of ether and 200 ml of petroleum ether to the RM, the target compound precipitates in crystalline form. It is filtered off, washed with petroleum ether and then dried in vacuo to yield the compound shown below of m.p. of 97–102° C.

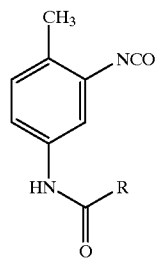

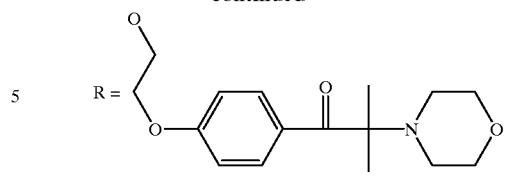

Examples A8, A9 and A10

Analogously to Example A6, the following compounds are prepared:

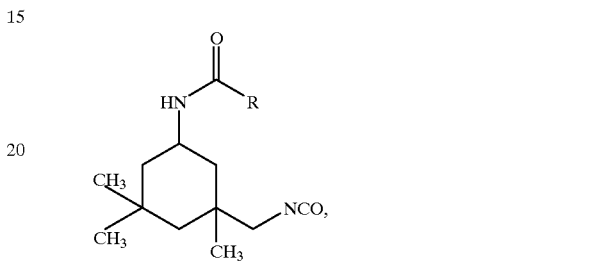

wherein R is one of the following radicals:

Example No. A8

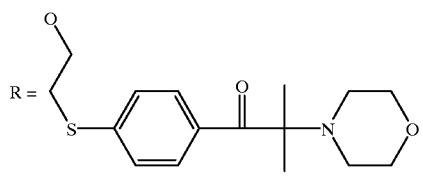

Example No. A9

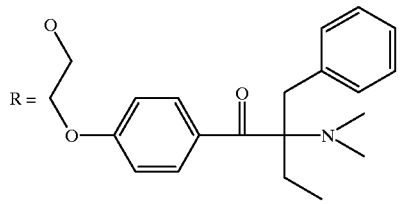

Example No. A10

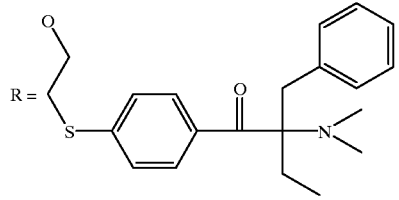

Example A11

Analogously to Example A6, the following compound is prepared:

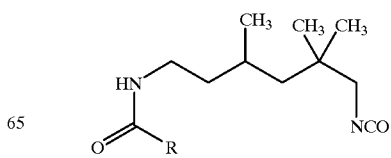

-continued

R = 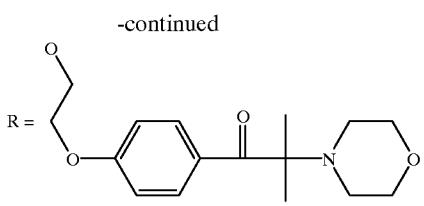

Example A12

Analogously to Example A6, the following isocyanate is prepared from 5.1 g (29.3 mmol) of 2,4-toluene diisocyanate (TDI) and 10 g (29.3 mmol) of 2-dimethylamino-2-benzyl-1-(4-(2-hydroxyethoxy)phenyl)-butan-1-one (from Example A1) using DBTDL as catalyst in methylene chloride. The RM is diluted with 500 ml of diethyl ether and 2 liters of petroleum ether, whereupon the product precipitates. It is filtered off, washed with diethyl ether/petroleum ether and dried in vacuo. A beige powder having a softening range of 99–103° C. is obtained.

Example A13

Preparation of

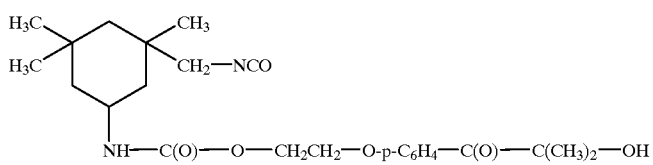

In a 500 ml flask equipped with reflux condenser, thermometer, stirrer and nitrogen inlet pipe, a solution of 11.125 g (0.05 mol) of freshly distilled isophorone diisocyanate (IPDI) in 50 ml of dry methylene chloride is mixed under nitrogen with a solution of 11.2 g (0.05 mol) of 4'-(β-hydroxyethoxy)-2-hydroxyprop-2-yl-phenone (Darocure 2959®) in 300 ml of dry methylene chloride and, after the addition of 20 mg of dibutyltin dilaurate as catalyst, the reaction mixture is stirred at room temperature for 48 hours. The course of the reaction is monitored by means of thin-layer chromatography on silica gel plates (60 $F_{254}$, Art. 5719 Merck) (eluant: toluene/acetonitrile 7:3). The resulting product is freed of small amounts of unreacted Darocure 2959 and di-substituted IPDI by column chromatography on silica gel 60 (eluant toluene/acetonitrile 7:3). After concentration of the pure fractions by evaporation using a rotary evaporator, a colourless oil is obtained which, upon cooling to −16° C., slowly crystallises and is then re-crystallised from dry diethyl ether. 15.6 g of a white crystalline product (70% of the theory) having a melting point of 76° C. are obtained.

The isocyanate content of the product is determined by titration with dibutylamine in toluene: calculated 2.242 mVal/g, found 2.25 mVal/g.

The method is described in "Analytical Chemistry of Polyurethanes" (High Polymer Series XVI/Part III, editors D. S. David & H. B. Staley, Interscience Publishers, New York 1969 p. 86).

Example A14

Preparation of

Analogously to Example A13, 10.5 g (0.05 mol) of 1,6-diisocyanato-2,2,4-trimethylhexane (IMDI) are reacted with 11.1 g (0.05 mol) of Darocure 2959® in 400 ml of dry methylene chloride for 40 hours at room temperature under nitrogen. 14.5 g (67% of the theory) of a white crystalline product of melting point 41–43° C. are obtained. NCO titration: calculated 2.30 mVal/g, found 2.36 mVal/g.

Example A15

Preparation of

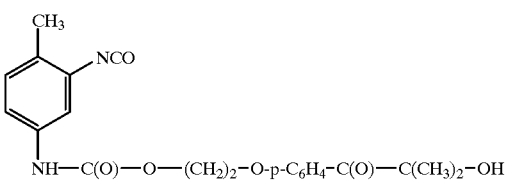

In the apparatus described in Example A13, 1.74 g (0.01 mol) of toluylene 2,4-diisocyanate (TDI) in 20 ml of dichloromethane are reacted with 2.24 g (0.01 mol) of Darocure 2959® dissolved in 60 ml of dry dichloromethane. Without the addition of a catalyst, the reaction mixture is stirred at room temperature for 48 hours and at 40° C. for 1 hour until no more unreacted Darocure 2959 can be detected in a thin-layer chromatogram. The product is isolated by precipitating the reaction solution in 180 ml of dry petroleum ether (b.p. 40–60° C.) and is then re-crystallised twice from dichloromethane/petroleum ether 1:3.

A white crystalline product having a melting point of 124–125° C. is obtained. Yield 17.2 g, corresponding to 87% of the theory. OCN titration: calculated 2.50 mVal/g, found 2.39 mVal/g.

B) Preparation of macrophotoinitiators

Example B1

Preparation of an oligomeric photoinitiator:

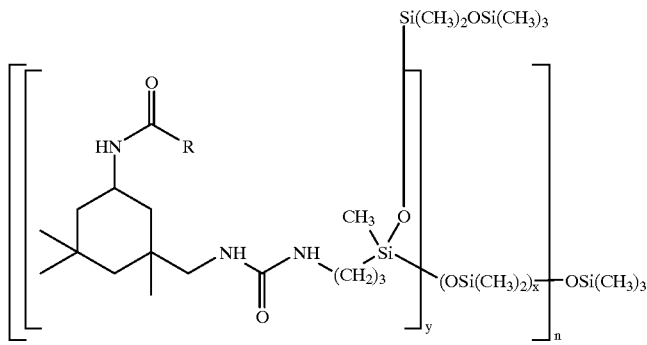

wherein

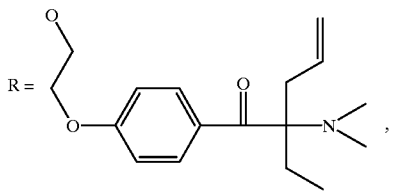

and x:y is approximately 27:1, and n is 5.

0.7 g (1.3 mmol) of the isocyanate from Example A6, 20 ml of dry methylene chloride and 2.55 g (0.51 mVal NH$_2$/g) of aminoalkylpolysiloxane KF 8003 (Shin Etsu, Japan) are placed in an apparatus according to Example A6. The reaction mixture is stirred at RT for 2 hours and at 40° C. for 20 minutes. The solvent is then removed using a RE. The residue is freed of solvent residues under a high vacuum (40° C., 0.001 mbar (0.1 Pa)). The title compound is obtained in quantitative yield. In the IR spectrum, there is no OCN band.

Example B2

Analogously to Example B1, an oligomeric photoinitiator having the structure according to Example B1 is prepared from 0.76 g (1.3 mmol) of isocyanate from Example A10 and 2.55 g (0.51 mVal NH$_2$/g) of aminoalkylpolysiloxane KF 8003 (Shin Etsu, Japan), wherein R has the following definition:

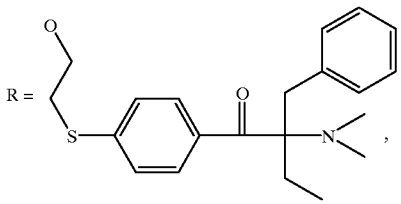

Example B3

Analogously to Example B1, an oligomeric photoinitiator having the following structure is prepared from 0.55 g (0.97 mmol) of isocyanate from Example A9 and 1.47 g (0.7 mVal NH$_2$/g) of aminoalkylpolysiloxane X-22-161B (Shin Etsu, Japan):

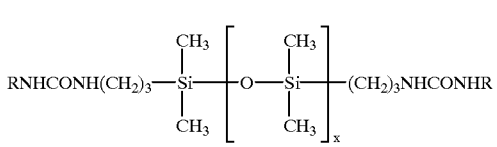

wherein x is approximately 38, and R corresponds to the radical of the title compound of Example A9 less the isocyanate.

Example B4

Analogously to Example B1, a solution of 1.0 g (1.95 mmol) of the isocyanate from Example A6 in 20 ml of dry acetonitrile is mixed with 2.24 g (0.84 mVal NH$_2$/g) of Jeffamin ED 2001 (Texaco, USA) in 30 ml of dry acetonitrile and the mixture is stirred at RT for 24 hours. After working up, 3.2 g (99%) of following photoinitiator are obtained:

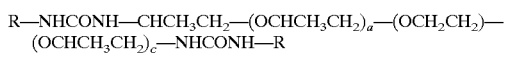

wherein a +c=2.5 and b=40.5, and R corresponds to the radical of the title compound of Example A6 less the isocyanate.

Example B5

In an apparatus according to Example A6, 1.65 g of polyvinyl alcohol (PVA) (Serva® 03/20, molecular weight approximately 13000) are dissolved at 80° C. under nitrogen in dry NMP. The solution is then cooled to RT and a solution of 1.0 g (1.88 mmol) of the isocyanate from Example A8 in 10 ml of dry NMP, and 5 mg of DBTDL as catalyst, are added thereto. This mixture is then heated at 40° C. for 48 hours. After that time, no OCN is detectable by IR at 2250 cm$^{-1}$. The RM is cooled to RT and 700 ml of diethyl ether are added thereto, the product precipitating. After filtration, washing with diethyl ether and then drying under a high vacuum, 1.9 g of a white product remain which, according to elemental analysis, comprises 2.20% S. Proton NMR is consistent with the following structure:

wherein n is approximately 10 and a:b=20:1; and R corresponds to the radical of the title compound of Example A8 less the isocyanate.

Examples B6, B7 and B8

Analogously to Example B5, two hydroxyalkyl-substituted polydimethylsiloxanes (KF-6002/KF-6001) and one dextran are reacted with the isocyanate from Example A8. The following parameters describe those compounds. The yields are approximately 90% in all cases. The sulfur content of those compounds is determined by combustion analysis (last column of the Table).

| isocyanate from Example A8 | OH-macromer | solvent | S-content (%) calc./found |
|---|---|---|---|
| 0.5 g (0.94 mmol) | KF-6002, Shin-Etsu, JP 1.5 g (0.63 Val OH/g) | THF | 1.50/1.38 |
| 0.5 g (0.94 mmol) | KF-6001, Shin-Etsu, JP 0.85 g (1.1 mVal OH/g) | THF | 2.22/2.08 |
| 0.5 g (0.94 mmol) | Dextran 8, Serva G 2.3 g, MW ≈ 8 – 12000 | DMSO | 1.08/0.99 |

Example B9

Analogously to Example B5, 3.23 g of collagen (Serva 17440, MW≈80000) are dissolved in DMSO over the course of 12 hours and then 1.0 g (1.9 mmol) of isocyanate from Example A9 in 10 ml of DMSO is added. After stilling the reaction mixture at RT for 72 hours, it is diluted with 500 ml of methanol, whereupon the product precipitates. The product is filtered off and washed repeatedly with dry THF. It is then dried under a high vacuum (0.1 Pa, RT, 72 hours). 2.8 g of a yellow-white product remain, the IR spectrum and proton NMR of which are consistent with the expected structure.

Example B10

Preparation of a polydimethylsiloxane that contains three pendant groups of the formula shown below:

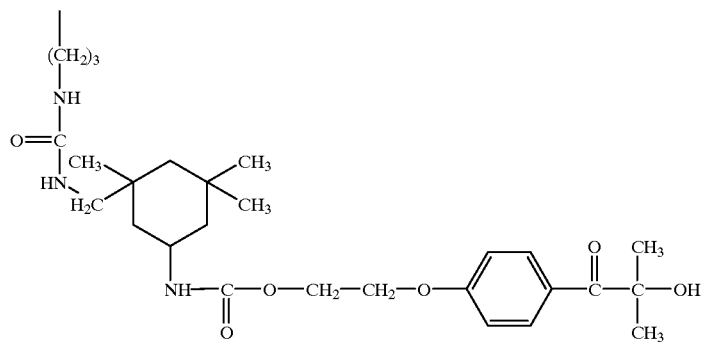

In a flask as described in Example A13, of 250 ml capacity, a solution of 1 g of the compound according to Example A13 (0.00224 mol) in 50 ml of dry dichloromethane is reacted with 4.37 g of aminoalkylpolysiloxane (0.515 mVal $NH_2$/g, Petrarch PS 813®: $\overline{M}n$~3000) dissolved in 100 ml of dry dichloromethane. The reaction mixture is stirred at room temperature for 10 hours and then heated at 40° C. for 1 hour. After cooling, the solvent is removed by concentration by evaporation using a rotary evaporator. A highly viscous, colourless oil is obtained which is finally freed of traces of the solvent under a high vacuum at 40° C. and $10^{-4}$ torr. Yield 5.34 g, corresponding to 99.5% of the theory. The product no longer exhibits an OCN band in the IR spectrum.

Examples B11–B15

Analogously to Example B10, other amino-functional macromers are reacted with the compound described in Example A13. The results are summarised in Table 3:

TABLE 3

| Example | amino-functional macromer | compound acc. to Ex. A13 | structure (product) | yield | % N (calculated/found) |
|---|---|---|---|---|---|
| B11 | X-22-161c (Shin Etsu, JP) 7.8 g (0.43 mVal $NH_2$/g) $\overline{M}$ ~ 4600 | 1.5 g (3.36 mmol) | a | 9.2 g (99.6%) | 1.52/1.42 |

TABLE 3-continued
| Example | amino-functional macromer | compound acc. to Ex. A13 | structure (product) | yield | % N (calculated/found) |
|---|---|---|---|---|---|
| B12 | Jeffamin ® T 403 (Texaco, USA) 2.8 g (6.38 mVal NH$_2$/g) | 2.84 g (6.36 mmol) | b | 5.62 g (99.7%) | 7.08/7.11 |
| B13 | Jaffamin ® D2000 (Texaco, USA 4.0 g (1 mVal NH$_2$/g) | 1.786 g (2.0 mmol) | c | 5.78 g (99.9%) | 2.90/2.89 |
| B14 | KF-8003 (Shin Etsu, JP) 4.6 g (0.49 mVal NH$_2$/g) | 1.0 g (2.29 mmol) | d | 4.55 g (98.9%) | 1.63/1.58 |
| B15 | X-22-161B (Shin Etsu, JP) 3.23 g (0.699 mVal NH$_2$/g) $\overline{M} \sim 2900$ | 1.0 g (2.29 mmol) | e | 4.2 g (99.3%) | 2.23/2.09 |
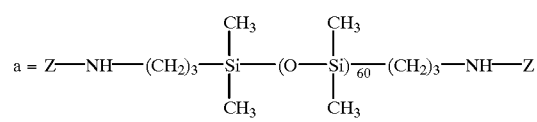
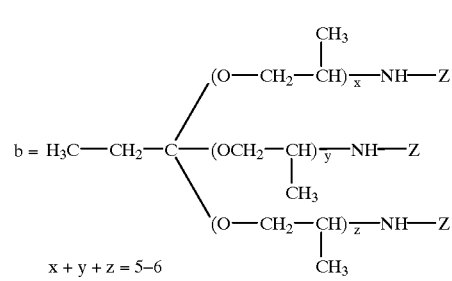
x + y + z = 5–6
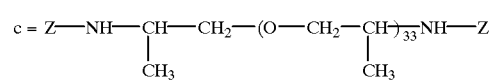
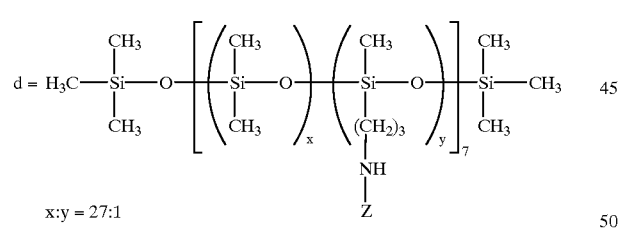
x:y = 27:1
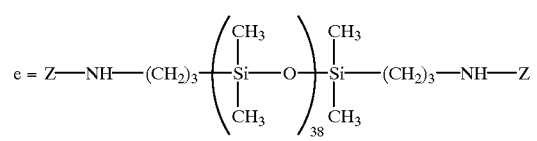
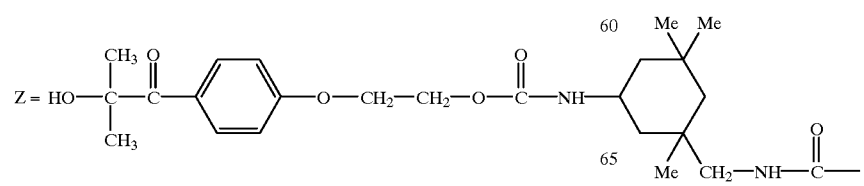

Example B16

Preparation of

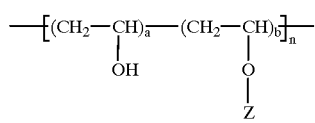

a:b ≈ 30:1
n ≈ 10

In the apparatus described in Example A13, 2.1 g of polyvinyl alcohol (PVA) (Serva® 03/20 $\overline{M}n$~13000) are dissolved at 90° C. under nitrogen in 50 ml of dry N-methyl-2-pyrrolidone (NMP). The solution is cooled to room temperature and filtered through a G4 glass frit. A solution of 0.7 g (1.567 mmol) of the compound according to Example A13 in 10 ml of dry NMP is then added thereto. After the addition of 10 mg of dibutyltin dilaurate, the reaction mixture is stirred at 50° C. for 48 hours. After that reaction time, no more unreacted isocyanate can be detected by IR spectroscopy (OCN at 2280 cm$^{-1}$). After cooling to room temperature, the product is precipitated in 400 ml of dry diethyl ether, filtered, washed with dry diethyl ether and dried in vacuo. 2.6 g of a white product that contains 1.38% nitrogen are obtained. $^1$H-chemical shifts of aromatic protons of the photoinitiators that are bonded to PVA: δ 7.00–7.10 (d, 2H); δ 8.15–8.25 (d, 2H).

Example B17

Reaction of hyaluronic acid with the reactive photoinitiator according to Example A13.

Analogously to Example B16, 444 mg of hyaluronic acid (Denki Kagaku Kogyo, $\overline{M}n$~1.2×10$^6$) dissolved in 100 ml of dry dimethyl sulfoxide (DMSO) are reacted at 50° C. with a solution of 200 mg of the compound described in Example A13 in 10 ml of dry DMSO. 534 mg (82.7% of the theory) of a white product are obtained that carries at approximately 30% of the sugar residues in the main chain of the polymer a photoinitiator group bonded as a urethane or a carboxylic acid amide, as shown by evaluation of the $^1$H-NMR spectrum.

$^1$H-chemical shifts of aromatic protons of the photoinitiators that are bonded to hyaluronic acid: δ 7.00–7.10 (d, 2H); δ 8.15–8.25 (d, 2H).

Examples B18–B20

Analogously to Example B17, the reactive photoinitiator described in Example A13 is reacted with a number of hydroxyalkyl-substituted polydimethylsiloxanes in dichloromethane as solvent. The results are given in Table 4.

TABLE 4

| Example | photoinitiator acc. to Ex. 1 | polysiloxane | yield | elemental analysis % calculated/found |
|---|---|---|---|---|
| B18 | 1.0 g (2.25 mmol) | KF-6002 (Shin Etsu, JP) 3.6 g (0.625 mVal OH/g) | 4.55 g (98.9%) | C 39.87/39.86 H 7.96/8.29 N 1.36/1.04 |
| B19 | 1.0 g (2.23 mmol) | KF-6001 (Shin Etsu, JP) 2.05 g (1.1 mVal OH/g) | 3.0 g (98.3%) | C 23.49/24.11 H 8.12/8.54 N 2.03/1.79 |
| B20 | 1.0 g (2.25 mmol) | gluconamidopropyl-methyldimethyl-siloxane copolymer 4.55 g (6.495 mVal OH/g) | 4.8 g (86.5%) | C —/36.18 H —/8.08 N —/1.03 |

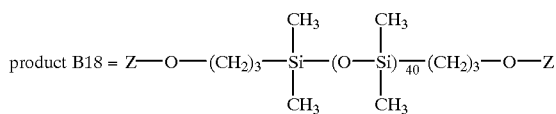

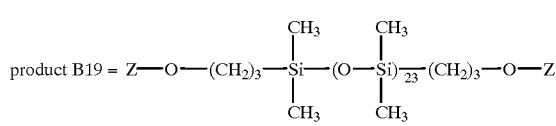

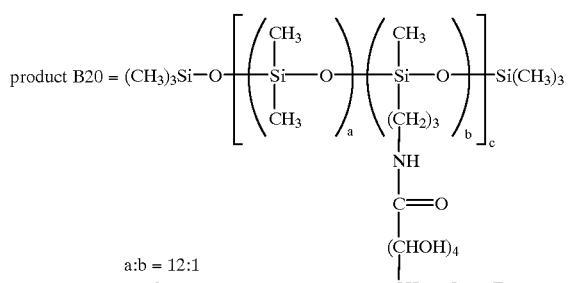

a:b = 12:1
c = 3

Example B21

Cyclodextrin macroinitiator
Cyclodextrins are cyclic oligosaccharides of the formula

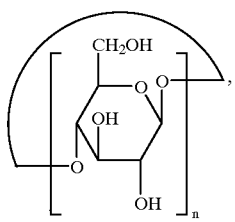

wherein n is a number from 6 to 8. They are commercially available and also hydroxyalkylated derivatives having a degree of substitution of from 0.6 to 1.6 per dextrin unit.

The reaction with the photoinitiators according to the invention generally produces mixtures that include derivatives having substitution patterns of various types and differing degrees of substitution. The preferred position for the substitution is the primary hydroxyl group. The mixtures can be separated by chromatography, derivatives mono-substituted at C$_6$ by from 6 to 8 photoinitiators being easily separated. In a 250 ml flask of brown glass equipped with reflux condenser, stirrer, internal thermometer and dropping funnel, 5 g (4.4053 mmol) of dry β-cyclodextrin and 0.094 g of dibutyltin dilaurate are dissolved under dry nitrogen in 50 ml of dry dimethyl sulfoxide. To this solution there is added dropwise at room temperature a solution of 13.77 g (3.084 mmol) of the compound according to Example A13 in 50 ml of dry dimethyl sulfoxide. The mixture is stirred first at room temperature for 3 hours and then at 50° C. for 15.5 hours. Thereafter, no more unreacted β-cyclodextrin is detectable by chromatography. The reaction mixture is cooled and the product is precipitated by the addition of 1000 ml of dry diethyl ether. The isolated viscous product is dissolved in 25 ml of acetone and again precipitated with 500 ml of diethyl ether, a white suspension being produced. The product is filtered off and the white powder obtained is washed twice with 100 ml of diethyl ether and then dried in vacua with the exclusion of light. 13.04 g (53.5% of the theory) of product are obtained The nitrogen content of 3.73% corresponds to an average degree of substitution of 5.6 per cyclodextrin ring.

The product is fractionated by flash-chromatography (column of 60 cm length, 5 cm diameter) on silica gel (Merck 60 F, particle size 0.04 to 0.063 mm) using methanol/toluene (2:8) as eluant. With 13 g of crude product, the following fractions are obtained, fraction 2 being eluted with methanol alone and fraction 3 with methanol/water (1:1):

| fraction | amount (g) | N content (%) | average degree of substitution |
|---|---|---|---|
| 1 | 1.3 | 4.25 | 6.4 |
| 2 | 3.59 | 3.59 | 5.4 |
| 3 | 1.36 | 1.36 | 2.0 |

The Production of Polymer Films and Contact Lenses

Example C1

5 g of poly(1,2-syndiotactic)-butadiene (PB) from Polysciences Inc. (Catalogue No. 16317, MW≈10 000) are dissolved at 40° C. in 100 ml of TBF. The solution is then cooled to RT and poured onto a Folanorm sheet (Folex®, Zürich, Switzerland) to produce a film of a PB solution of approximately 0.5 mm thickness. The THF is slowly evaporated at RT under nitrogen. The polybutadiene film which remains is then extracted with ethanol and dried until its weight is constant.

Example C2

2.2 g of PB are dissolved in 50 ml of methylcyclohexane at 40° C. under nitrogen. A solution of 2 g of H-siloxane (Experimental Product K-3272, Goldschmidt, Germany) in 5 ml of methylcyclohexane is added thereto and stirring is carried out for 5 minutes. This solution is then gassed with nitrogen for 30 minutes. There are then added to this solution 3 drops of the catalyst platinum divinyltetramethyldisiloxane (ABCR, PC 072) dissolved in 1 ml of methylcyclohexane and the mixture is then heated at 50° C., with stirring, for 3 minutes. This mixture is then placed between two glass plates to produce a liquid film of approximately 1.5 mm thickness. This sandwich system is then heated at 60° C. under nitrogen for 16 hours. It is then cooled to RT, the glass plates are removed and the crosslinked polybutadiene film is extracted with THF. After extraction, the crosslinked polybutadiene film is dried until its weight is constant.

Example C3

5.35 g (1 mmol) of vinyl-containing polysiloxane (Silopren U Additiv V 200, Bayer Leverkusen, Germany) are mixed with 1.13 g (2 mmol) of H-siloxane (Experimental Product 1085, Goldschmidt, Germany) and the mixture is stirred at RT under reduced pressure (200 mbar (20kPa)) for one hour. Nitrogen is then bubbled through the mixture for 30 minutes, 2 drops of the catalyst platinum divinyltetramethyldisiloxane (ABCR, PC 072) are added and the mixture is stirred for 5 minutes. Polypropylene moulds (Ciba Vision Atlanta, suitable for the production of a moulded article having a thickness of 0.5 mm and a diameter of 1 cm) are then filled with this mixture, closed and heated in an oven at 60° C. under nitrogen for 16 hours. The moulds are allowed to cool to RT and are opened, and the disks so produced, which contain crosslinked polyvinylsiloxane, are extracted with ethanol and subsequently dried until their weight is constant.

Example C4

Contact lenses consisting of crosslinked polyvinylsiloxane are produced analogously to Example C3, using polypropylene moulds suitable for the production of soft contact lenses having a thickness of 100 μm, a diameter of 1.4 cm and a base curve of 8.4 mm.

Example C5

2.63 g (0.5 mmol) of vinyl-containing polysiloxane (Silopren U Additiv V 200) and 3.0 g of H-siloxane (Experimental Product K 3272, Goldschmidt, Germany) are mixed and stirred at RT under reduced pressure (200 mbar (20 kPa)) for one hour. Nitrogen is then bubbled through the mixture for 30 minutes, 2 drops of the catalyst platinum divinyltetramethyldisiloxane (ABCR, PC 072) are added and the mixture is stirred for 10 minutes. Polypropylene contact lens moulds (Ciba Vision Atlanta, USA) are then filled with this mixture, closed and heated in an oven at 60° C. under nitrogen for 16 hours. The moulds are allowed to cool to RT and are opened, and the contact lenses so produced, which contain crosslinked polyvinylsiloxane, are extracted with ethanol and subsequently dried until their weight is constant.

Example D1

4 g of photoinitiator from Example A6 are dissolved under nitrogen in 10 ml of acetone. A portion of this solution is sprayed onto a polybutadiene film according to Example C1, so that, after the acetone has been evaporated while flushing with nitrogen, an even photoinitiator film is produced on the polybutadiene film. The coated polybutadiene film is then irradiated with UV light (12 mW/cm$^2$) for 10 minutes. The film is subsequently washed three times with acetone in order to remove non-bonded photoinitiator. The film is then dried under reduced pressure (0.001 bar (0.1 Pa)) until its weight is constant. The Fourier-transform IR spectrum (FT-IR) of the film exhibits an OCN band at 2250 cm$^{-1}$. Finally, the film is immersed for 2 hours in a 5% Jeffamin M 2070 solution in acetone and is then thoroughly washed twice with acetone and three times with deionised water. The polybutadiene film so coated is analysed in FT-IR and then the contact angles are determined (K 12, Kruss GmbH, Hamburg, Germany).

| | contact angle in [°] | |
|---|---|---|
| polybutadiene film C1 | advancing | receding |
| uncoated | 102 | 78 |
| coated | 66 | 47 |

Example D2

Analogously to Example D1, a crosslinked polybutadiene film from Example C2 is coated.

| polybutadiene film C2 | contact angle in [°] | |
|---|---|---|
| | advancing | receding |
| uncoated | 111 | 71 |
| coated | 96 | 59 |

Example D3

Analogously to Example D1, a polybutadiene film from Example C1 is coated with the photoinitiator from Example A8.

| polybutadiene film C1 | contact angle in [°] | |
|---|---|---|
| | advancing | receding |
| uncoated | 102 | 78 |
| coated | 62 | 46 |

Example D4

Analogously to Example D1, lenses from Example C4 are coated with the photoinitiator from Example A8.

| polyvinylsiloxane C4 | contact angle in [°] | |
|---|---|---|
| | advancing | receding |
| uncoated | 111 | 78 |
| coated | 98 | 34 |

Example D5

Analogously to Example D1, a crosslinked polyvinylsiloxane disk from Example C3 is coated with the photoinitiator from Example A6.

| disk from C3 | contact angle in [°] | |
|---|---|---|
| | advancing | receding |
| uncoated | 112 | 72 |
| coated | 99 | 38 |

Example D6

Analogously to Example D1, a polybutadiene film according to Example C1 is coated with the photoinitiator from Example A6. In contrast to Example D1, however, this film is then immersed in a DMSO solution comprising 1% Dextran 8 (Serva) and approximately 1 mg of DBTDL as catalyst.

| polybutadiene film C1 | contact angle in [°] | |
|---|---|---|
| | advancing | receding |
| uncoated | 102 | 78 |
| coated | 98 | 51 |

Example D7

Analogously to Example D1, a polybutadiene film according to Example C1 is coated with the photoinitiator from Example A6. In contrast to Example D1, however, this film is then immersed in an aqueous solution comprising 5% polyethyleneimine (Fluka).

| polybutadiene film C1 | contact angle in [°] | |
|---|---|---|
| | advancing | receding |
| uncoated | 102 | 78 |
| coated | 66 | 18 |

Example D8

Analogously to Example D1, contact lenses according to Example C5 are coated with the photoinitiator from Example A6. In constrast to Example D1, however, these lenses are then immersed in an aqueous solution comprising 5% polyethyleneimine (Fluka).

| contact lenses from C5 | contact angle in [°] | |
|---|---|---|
| | advancing | receding |
| uncoated | 115 | 80 |
| coated | 99 | 56 |

Example E1

2 g of the macrophotoinitiator according to Example B5 are dissolved in 50 ml of dry DMSO. Nitrogen is bubbled through this solution for 30 minutes. A polybutadiene film from Example C1 (2×2 cm) is then immersed in this solution for 10 minutes, then removed and irradiated with UV light (12 mW/cm$^2$) for 10 minutes. The film so coated is washed once with DMSO, twice with isopropanol, once with 50% aqueous isopropanol and once with water. The film is then dried and analysed (layer thickness of the hydrophilic film is approximately 6 μm, determined by means of optical microscopy and RuO$_4$ contrasting.

| polybutadiene film C1 | contact angle in [°] | |
|---|---|---|
| | advancing | receding |
| uncoated | 102 | 78 |
| coated | 48 | 37 |

Example E2

Analogously to Example E1, a crosslinked polybutadiene film from Example C2 is treated with the macrophotoinitiator from Example B5.

| polybutadiene film C2 | contact angle in [°] | |
|---|---|---|
| | advancing | receding |
| uncoated | 111 | 71 |
| coated | 97 | 38 |

Example E3

Analogously to Example E1, siloxane disks from Example C3 are treated with the macrophotoinitiator from Example B8.

| siloxane disks from C3 | contact angle in [°] | |
|---|---|---|
| | advancing | receding |
| uncoated | 112 | 72 |
| coated | 94 | 36 |

Example E4

Analogously to Example E1, contact lenses from Example C4 are treated with the macrophotoinitiator from Example B5.

| contact lenses from C4 | contact angle in [°] | |
|---|---|---|
| | advancing | receding |
| uncoated | 111 | 78 |
| coated | 88 | 37 |

Example E5

Analogously to Example E1, contact lenses from Example C5 are treated with the macrophotoinitiator from Example B8.

| contact lenses from C5 | contact angle in [°] | |
|---|---|---|
| | advancing | receding |
| uncoated | 115 | 70 |
| coated | 76 | 41 |

What is claimed is:

1. A process for the multi-stage coating of a surface, which comprises, on the one hand, covalently bonding a functional photoinitiator containing at least one isocyanate group, or a macroinitiator derived therefrom, to a carrier and, on the other hand, covalently bonding an oligomer or polymer, forming a new surface layer, to the functional photoinitiator or to the carrier modified by a functional photoinitiator via functional groups that are co-reactive with isocyanate groups, wherein said process comprises the following steps:

(a) reacting an oligomer or polymer containing groups that are co-reactive with isocyanate groups with a functional photoinitiator of formula Ia or Ib to form a macroinitiator, the isocyanate group of the photoinitiator forming a covalent bond with one of the co-reactive groups of the oligomer or polymer, (b) applying a thin layer of the macroinitiator so obtained to a surface containing suitable groups that are co-reactive with radicals;

(c) irradiating the coated surface with UV light of a suitable wavelength, there being produced by radical ($\alpha$-cleavage in the macroinitiator benzoyl-like radicals that form a covalent bond with the co-reactive groups of the surface;

wherein formulae Ia and Ib are as follows:

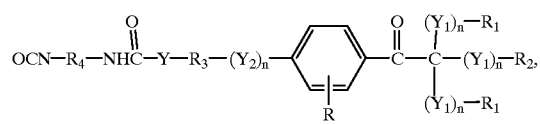

(Ia)

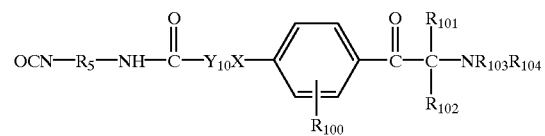

(Ib)

wherein Y is O, NH or $NR_{1A}$;

$Y_1$ is O;

$Y_2$ is —O—, —O—(O)C—, —C(O)—O— or —O—C(O)—O—;

each n independently of the others is 0 or 1;

R is H, $C_1$–$C_{12}$alkyl, $C_1$–$C_{12}$alkoxy or $C_1$–$C_{12}$alkylNH—;

$R_1$ and $R_2$ are each independently of the other H, linear or branched $C_1$–$C_8$alkyl, $C_1$–$C_8$hydroxyalkyl or $C_6$–$C_{10}$aryl, or two groups $R_1$—$(Y_1)_n$— together are —$(CH_2)_x$—, or the groups $R_1$—$(Y_1)_n$— and $R_2$—$(Y_1)_n$— together are a radical of the formula

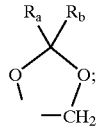

$R_3$ is a direct bond or linear or branched $C_1$–$C_8$alkylene that is unsubstituted or substituted by —OH and/or optionally interrupted by one or more groups —O—, —O—C(O)— or —O—C(O)—O—;

$R_4$ is branched $C_3$–$C_{18}$alkylene, unsubstituted or $C_1$–$C_4$alkyl- or $C_1$–$C_4$alkoxy-substituted $C_6$–$C_{10}$arylene, or unsubstituted or $C_1$–$C_4$alkyl- or $C_1$–$C_4$alkoxy-substituted $C_7$–$C_{18}$-aralkylene, unsubstituted or $C_1$–$C_4$alkyl- or $C_1$–$C_4$alkoxy-substituted $C_3$–$C_8$cycloalkylene, unsubstituted or $C_1$–$C_4$alkyl- or $C_1$–$C_4$alkoxy-substituted $C_3$–$C_8$cycloalkylene-$C_yH_{2y}$- or unsubstituted or $C_1$–$C_4$alkyl- or $C_1$–$C_4$alkoxy-substituted-$C_yH_{2y}$-($C_3$–$C_8$cycloalkylene)-$C_yH_{2y}$—;

$R_5$ independently has the same definitions as $R_4$ or is linear $C_3$–$C_{18}$alkylene; $R_{1A}$ is lower alkyl;

x is an integer from 3 to 5;

y is an integer from 1 to 6;

$R_a$ and $R_b$ are each independently of the other H, $C_1$–$C_8$alkyl, $C_3$–$C_8$cycloalkyl, benzyl or phenyl;

with the provisos that n in the groups —$(Y_1)_n$—$R_1$ is 0 when $R_2$ is H; that not more than two $Y_1$ of the —$(Y_1)_n$— groups are 0 and n in the other —$(Y_1)_n$— groups is 0; and that n in the group —$(Y_2)_n$— is 0 when $R_3$ is a direct bond;

and wherein also X is bivalent —O—, —NH—, —S—, lower alkylene or

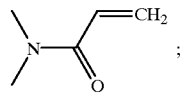

$Y_{10}$ is a direct bond or —O(CH$_2$)y— wherein y is an integer from 1 to 6 and the terminal CH$_2$ group of which is linked to the adjacent X in formula (Ib);

$R_{100}$ is H, $C_1$–$C_{12}$alkyl, $C_1$–$C_{12}$alkoxy, $C_1$-CalkylNH— or —NR$_{1A}$R$_{1B}$ wherein R$_{1A}$ is lower alkyl and R$_{1B}$ is H or lower alkyl;

$R_{101}$, is linear or branched lower alkyl, lower alkenyl or aryl-lower alkyl;

$R_{102}$ independently of $R_{101}$, has the same definitions as $R_{101}$, or is aryl, or $R_{101}$, and $R_{102}$ together are, —(CH$_2$)$_m$— wherein m is an integer from 2 to 6;

$R_{103}$ and $R_{104}$ are each independently of the other linear or branched lower alkyl that may be substituted by $C_1$–$C_4$alkoxy, or aryl-lower alkyl or lower alkenyl; or $R_{103}$ and $R_{104}$ together are —(CH$_2$)$_s$—Y$_{11}$—(CH$_2$)$_z$— wherein Y$_{11}$ is a direct bond, —O—, —S— or —NR$_{1B}$—, and R$_{1B}$ is H or lower alkyl and each z independently of the other is an integer from 2 to 4.

2. A process according to claim 1, wherein there is used as functional photoinitiator a compound of formula Ia or Ib

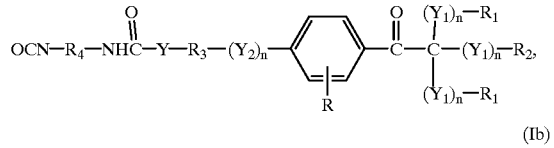

(Ia)

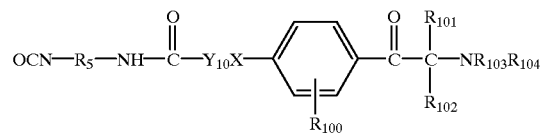

(Ib)

wherein Y is O, NH or NR$_{1A}$;
Y, is O;
Y$_2$ is —O—, —O—(O)C—, —C(O)—O— or —O—C(O)—O—;
each n independently of the others is 0 or 1;
R is H, $C_1$–$C_{12}$alkyl, $C_1$–$C_{12}$alkoxy or $C_1$–$C_{12}$alkylNH—;
R$_1$ and R$_2$ are each independently of the other H, linear or branched $C_1$–$C_8$alkyl, $C_1$–$C_8$hydroxyalkyl or $C_6$–$C_{10}$aryl, or
two groups R$_1$—(YI)$_n$— together are —(CH$_2$)$_x$—, or the groups R$_1$—(YI)$_n$— and R$_2$—(YI)$_n$— together are a radical of the formula

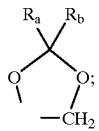

$R_3$ is a direct bond or linear or branched $C_1$–$C_8$alkylene that is unsubstituted or substituted by —OH and/or optionally interrupted by one or more groups —O—, —O—C(O)— or —O—C(O)—O—;

$R_4$ is branched $C_3$–$C_{18}$alkylene, unsubstituted or $C_1$–$C_4$alkyl- or $C_1$–$C_4$alkoxy-substituted $C_6$–$C_{10}$arylene, or unsubstituted or $C_1$–$C_4$alkyl- or $C_1$–$C_4$alkoxy-substituted $C_7$–$C_{18}$-aralkylene, unsubstituted or $C_1$–$C_4$alkyl- or $C_1$–$C_4$alkoxy-substituted $C_3$–$C_8$cycloalkylene, unsubstituted or $C_1$–$C_4$alkyl- or $C_1$–$C_4$alkoxy-substituted $C_3$–$C_8$cycloalkylene-C$_y$H$_{2y}$- or unsubstituted or $C_1$–$C_4$alkyl- or $C_1$–$C_4$alkoxy-substituted-C$_y$H$_{2y}$-(C$_3$–C$_8$cycloalkylene)-C$_y$H$_{2y}$—;

$R_5$ independently has the same definitions as $R_4$ or is linear $C_3$–$C_{18}$alkylene;

$R_{1A}$ is lower alkyl;

x is an integer from 3 to 5;

y is an integer from 1 to 6;

$R_a$ and $R_b$ are each independently of the other H, $C_1$–$C_8$alkyl, $C_3$–$C_8$-cycloalkyl, benzyl or phenyl;

with the provisos that n in the groups —$(Y_1)_n$—$R_1$ is 0 when $R_2$ is H; that not more than two $Y_1$ of the —$(Y_1)_n$— groups are 0 and n in the other —$(Y_1)_n$— groups is 0; and that n in the group —$(Y_2)_n$— is 0 when $R_3$ is a direct bond;

and wherein also X is bivalent —O—, —NH—, —S—, lower alkylene or

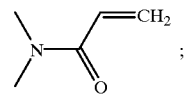

$Y_{10}$ is a direct bond or —O—(CH$_2$)y— wherein y is an integer from 1 to 6 and the terminal CH$_2$ group of which is linked to the adjacent X in formula (Ib);

$R_{100}$ is H, $C_1$–$C_{12}$alkyl, $C_1$–$C_{12}$alkoxy, $C_1$-CalkylNH— or —NR$_{1A}$R$_{1B}$ wherein R$_{1A}$ is lower alkyl and R$_{1B}$ is H or lower alkyl;

$R_{101}$, is linear or branched lower alkyl, lower alkenyl or aryl-lower alkyl;

$R_{102}$ independently of $R_{101}$, has the same definitions as $R_{101}$, or is aryl, or $R_{101}$, and $R_{102}$ together are, —(CH$_2$)$_m$— wherein m is an integer from 2 to 6;

$R_{103}$ and $R_{104}$ are each independently of the other linear or branched lower alkyl that may be substituted by $C_1$–$C_4$alkoxy, or aryl-lower alkyl or lower alkenyl; or $R_{103}$ and $R_{104}$ together are —(CH$_2$)$_s$—Y$_{11}$—(CH$_2$)$_z$— wherein Y$_{11}$ is a direct bond, —O—, —S— or —NR$_{1B}$—, and R$_{1B}$ is H or lower alkyl and each z independently of the other is an integer from 2 to 4.

3. A process according to claim 1, wherein there is used as macroinitiator an oligomer or polymer that has one or more H-active —OH and/or —NH— groups bonded terminally or pendantly, if desired via one or more bridge groups, the H atoms of which H-active groups are partly or completely substituted by radicals $R_{200}$, wherein $R_{200}$ is a radical of formula IVa or IVb

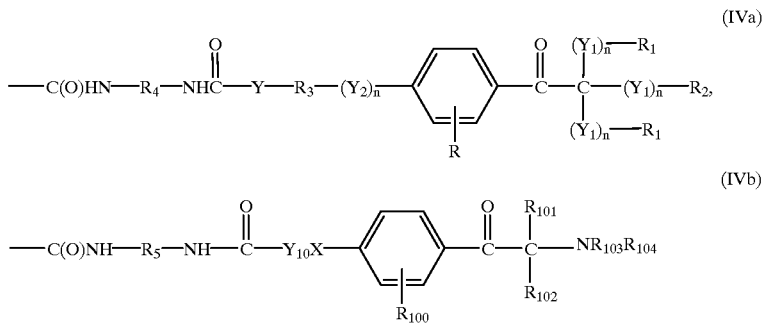

wherein X, Y, $Y_1$, $Y_2$, $Y_{10}$, R, $R_1$, $R_2$, $R_3$, $R_4$, $R_5$, $R_{100}$, $R_{101}$, $R_{102}$, $R_{103}$, $R_{104}$ and n are as defined in claim 2.

4. A process according to claim 1, wherein the oligomer or polymer is a natural or synthetic oligomer or polymer.

5. A process according to claim 4, wherein there is understood by a natural oligomer or polymer a cyclodextrin, a starch, hyaluronic acid, deacetylated hyaluronic acid, chitosan, trehalose, cellobiose, maltotriose, maltohexaose, chitohexaose, agarose, chitin 50, amylose, a glucane, heparin, xylan, pectin, galactan, poly-galactosamine, a glycosaminoglycane, dextran, aminated dextran, cellulose, a hydroxyalkylcellulose, a carboxyalkylcellulose, fucoidan, chondroitin sulfate, a sulfated polysaccharide, a mucopolysaccharide, gelatin, zein, collagen, albumin, globulin, bilirubin, ovalbumin, keratin, fibronectin or vitronectin, pepsin, trypsin or lysozyme; and by a synthetic oligomer or polymer a polymer or hydrolysed polymer of one or more vinyl esters or ethers (polyvinyl alcohol); a polydiolefin or hydroxylated polydiolefin, e.g. polybutadiene, polyisoprene or chloroprene; polyacrylic acid or polymethacrylic acid or a polyacrylate, polymethacrylate, polyacrylamide or polymethacrylamide, if desired having hydroxyalkyl or aminoalkyl radicals in the ester group or amide group; a polysiloxane, if desired having hydroxyalkyl or aminoalkyl groups; a polyether of one or more epoxides or glycidyl compounds and diols; a polyvinylphenol or a copolymer of vinylphenol and one or more olefinic comonomers; or a copolymer of at least one monomer from the group vinyl alcohol, vinyl-pyrrolidone, acrylic acid, methacrylic acid, or a hydroxyalkyl- or aminoalkyl-containing acrylate, methacrylate, or acrylamide or methacrylamide, or a diolefin or hydroxylated diolefin with one or more ethylenically unsaturated comonomers, e.g. acrylonitrile, an olefin, a diolefin, vinyl chloride, vinylidene chloride, vinyl fluoride, vinylidene fluoride, styrene, α-methylstyrene, a vinyl ether or a vinyl ester, or a polyoxaalkylene, if desired having terminal OH or aminoalkyloxy groups.

6. A process according to claim 1, wherein the photoinitiator used is selected from

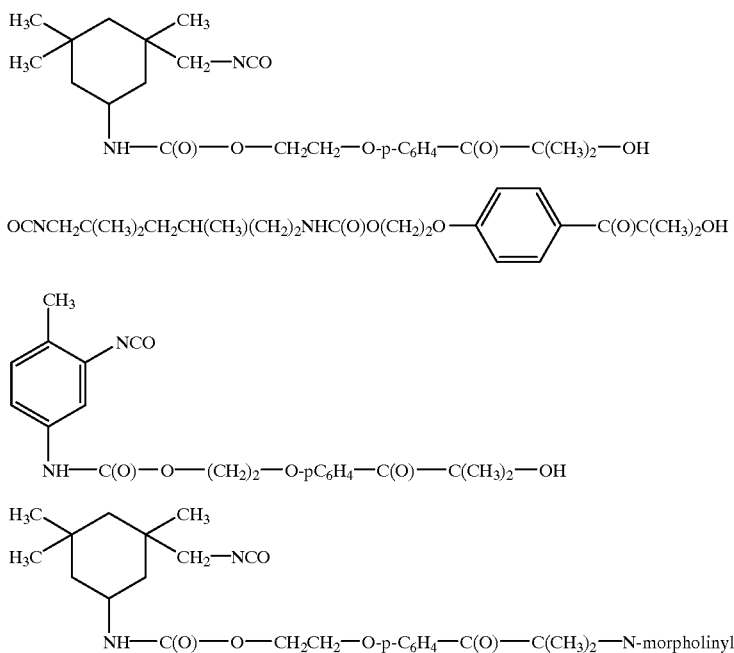

-continued

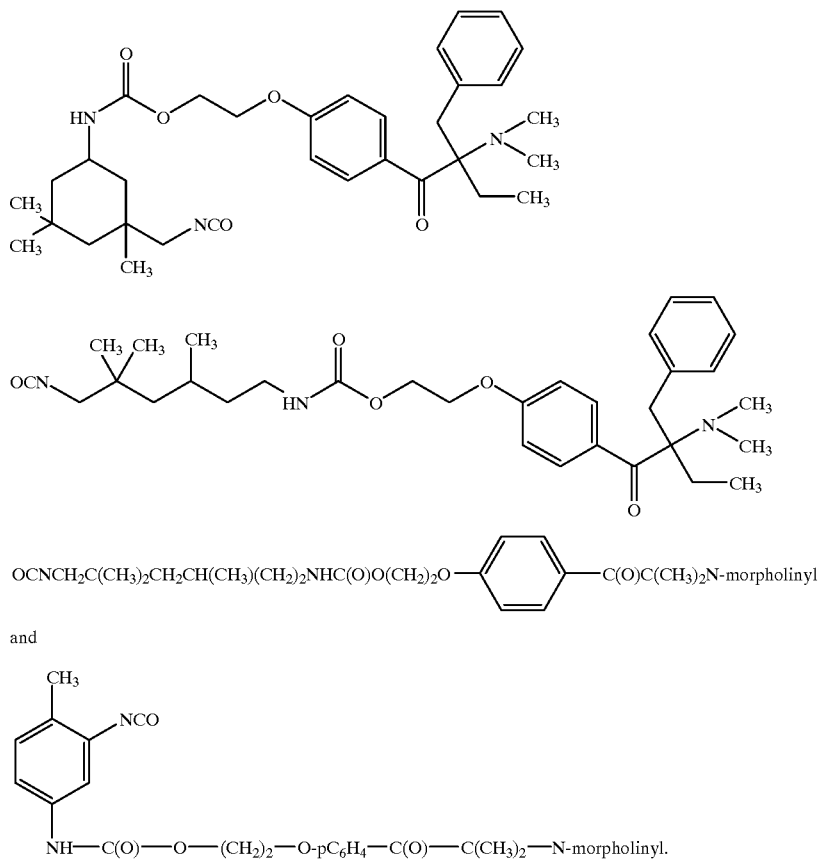

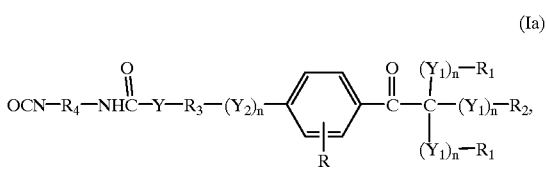

and

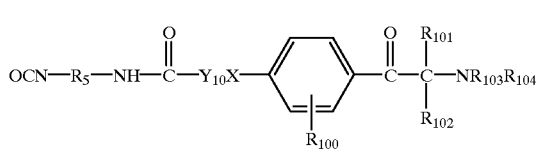

7. A process according to claim 1 wherein the surface is the surface of a contact lens or an ophthalmic moulded article.

8. A coated base material produced according to the process of claim 1.

9. A coated film produced according to the process of claim 1.

10. A coated contact lens produced according to the process of claim 1.

11. A process for the multi-stage coating of a surface, which comprises, on the one hand, covalently bonding a functional photoinitiator containing at least one isocyanate group, or a macroinitiator derived therefrom, to a carrier and, on the other hand, covalently bonding an oligomer or polymer, forming a new surface layer, to the functional photoinitiator or to the carrier modified by a functional photoinitiator via functional groups that are co-reactive with isocyanate groups, wherein said process comprises the following steps:

(a) where applicable providing the surface of a base material with functional groups that are co-reactive with isocyanate groups, for example OH, $NH_2$ or COOH, by suitable chemical or physical pre-treatment, for example plasma treatment;

(b) covering the surface containing groups that are co-reactive with isocyanate groups with a functional photoinitiator of formula Ia or Ib, the isocyanate group of the photoinitiator forming a covalent bond with the surface;

(c) covering the surface modified by a photoinitiator with a thin layer of a vinylic monomer containing at least one isocyanate group or a mixture, of vinyl monomers containing such a monomer, (d) irradiating the coated surface with UV light of a suitable wavelength, there being produced a graft (co) polymer containing isocyanate, groups that is covalently bonded to the surface;

(e) applying to the surface so modified an oligomer or polymer containing groups that are co-reactive with isocyanate groups;

(f) a covalent bond being formed by the oligomer or polymer with the isocyanate groups of the graft (co) polymer;

wherein formulae Ia and Ib are as follows:

(Ia)

OCN—$R_4$—NHC(O)—Y—$R_3$—$(Y_2)_n$—[ring]—C(O)—C(R)((Y_1)_n—$R_1$)((Y_1)_n—$R_2$)((Y_1)_n—$R_1$), (Ib)

OCN—$R_5$—NH—C(O)—$Y_{10}$X—[ring with $R_{100}$]—C(O)—C($R_{101}$)($R_{102}$)—$NR_{103}R_{104}$ wherein Y is O, NH or $NR_{1A}$;
$Y_1$ is O;
$Y_2$ is —O—, —O—(O)C—, —C(O)—O— or —O—C(O)—O—;

each n independently of the others is 0 or 1;

R is H, $C_1$–$C_{12}$alkyl, $C_1$–$C_{12}$alkoxy or $C_1$–$C_{12}$alkylNH—;

$R_1$ and $R_2$ are each independently of the other H, linear or branched $C_1$–$C_8$alkyl, $C_1$–$C_8$hydroxyalkyl or $C_6$–$C_{10}$aryl, or two groups $R_1$—$(Y_1)_n$— together are —$(CH_2)_x$—, or the groups $R_1$—$(Y_1)_n$— and $R_2$—$(Y_1)_n$— together are a radical of the formula

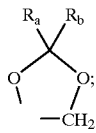

$R_3$ is a direct bond or linear or branched $C_1$–$C_8$alkylene that is unsubstituted or substituted by —OH and/or optionally interrupted by one or more groups —O—, —O—C(O)— or —O—C(O)—O—;

$R_4$ is branched $C_3$–$C_{18}$alkylene, unsubstituted or $C_1$–$C_4$alkyl- or $C_1$–$C_4$alkoxy-substituted $C_6$–$C_{10}$arylene, or unsubstituted or $C_1$–$C_4$alkyl- or $C_1$–$C_4$alkoxy-substituted $C_7$–$C_{18}$-aralkylene, unsubstituted or $C_1$–$C_4$alkyl- or $C_1$–$C_4$alkoxy-substituted $C_3$–$C_8$cycloalkylene, unsubstituted or $C_1$–$C_4$alkyl- or $C_1$–$C_4$alkoxy-substituted $C_3$–$C_8$cycloalkylene-$C_yH_{2y}$- or unsubstituted or $C_1$–$C_4$alkyl- or $C_1$–$C_4$alkoxy-substituted-$C_yH_{2y}$-($C_3$–$C_8$cycloalkylene)-$C_yH_{2y}$—;

$R_5$ independently has the same definitions as $R_4$ or is linear $C_3$–$C_{18}$alkylene; $R_{1A}$ is lower alkyl;

x is an integer from 3 to 5;

y is an integer from 1 to 6;

$R_a$ and $R_b$ are each independently of the other H, $C_1$–$C_8$alkyl, $C_3$–$C_8$cycloalkyl, benzyl or phenyl;

with the provisos that n in the groups —$(Y_1)_n$—$R_1$ is 0 when $R_2$ is H; that not more than two $Y_1$ of the —$(Y_1)_n$— groups are 0 and n in the other —$(Y_2)_n$— groups is 0; and that n in the group —$(Y_2)_n$— is 0 when $R_3$ is a direct bond;

and wherein also X is bivalent —O—, —NH—, —S—, lower alkylene or

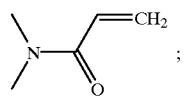

$Y_{10}$ is a direct bond or —O($CH_2$)$_y$— wherein y is an integer from 1 to 6 and the terminal $CH_2$ group of which is linked to the adjacent X in formula (Ib);

$R_{100}$ is H, $C_1$–$C_{12}$alkyl, $C_1$–$C_{12}$alkoxy, $C_1$-CalkylNH— or —$NR_{1A}R_{1B}$ wherein $R_{1A}$ is lower alkyl and $R_{1B}$ is H or lower alkyl;

$R_{101}$, is linear or branched lower alkyl, lower alkenyl or aryl-lower alkyl;

$R_{102}$ independently of $R_{101}$, has the same definitions as $R_{101}$, or is aryl; or $R_{101}$, and $R_{102}$ together are, —$(CH_2)_m$— wherein m is an integer from 2 to 6;

$R_{103}$ and $R_{104}$ are each independently of the other linear or branched lower alkyl that may be substituted by $C_1$–$C_4$alkoxy, or aryl-lower alkyl or lower alkenyl; or $R_{103}$ and $R_{104}$ together are —$(CH_2)_z$—$Y_{11}$—$(CH_2)_z$— wherein $Y_{11}$ is a direct bond, —O—, —S— or —$NR_{1B}$, and $R_{1B}$ is H or lower alkyl and each z independently of the other is an integer from 2 to 4.

12. A modified base material according to claim 11, which is a film.

13. A modified base material according to claim 11, which is a contact lens.

14. A film comprising (a) a base material and (b) a covalently bonded thin layer on the surface, consisting of (b1) constituents that are derived from at least one photoinitiator of formula Ia or Ib and (b2) a polymer of an olefin that is covalently bonded to isocyanate groups of constituent (b1) via groups that are co-reactive with isocyanate groups, wherein formulae Ia and Ib are as follows:

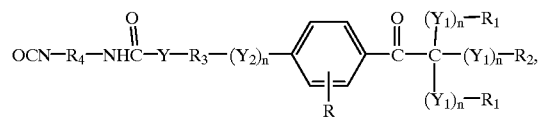

(Ia)

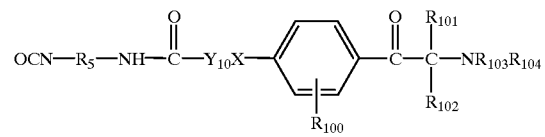

(Ib)

wherein Y is O, NH or $NR_{1A}$;

$Y_1$ is O;

$Y_2$ is —O—, —O—(O)C—, —C(O)—O— or —O—C(O)—O—;

each n independently of the others is 0 or 1;

R is H, $C_1$–$C_{12}$alkyl, $C_1$–$C_{12}$alkoxy or $C_1$–$C_{12}$alkylNH—;

$R_1$ and $R_2$ are each independently of the other H, linear or branched $C_1$–$C_8$alkyl, $C_1$–$C_8$hydroxyalkyl or $C_6$–$C_{10}$aryl, or two groups $R_1$—$(Y_1)_n$— together are —$(CH_2)_x$—, or the groups $R_1$—$(Y_1)_n$— and $R_2$—$(Y_1)_n$— together are a radical of the formula

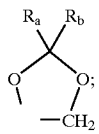

$R_3$ is a direct bond or linear or branched $C_1$–$C_8$alkylene that is unsubstituted or substituted by —OH and/or optionally interrupted by one or more groups —O—, —O—C(O)— or —O—C(O)—O—;

$R_4$ is branched $C_3$–$C_{18}$alkylene, unsubstituted or $C_1$–$C_4$alkyl- or $C_1$–$C_4$alkoxy-substituted $C_6$–$C_{10}$arylene, or unsubstituted or $C_1$–$C_4$alkyl- or $C_1$–$C_4$alkoxy-substituted $C_7$–$C_{18}$-aralkylene, unsubstituted or $C_1$–$C_4$alkyl- or $C_1$–$C_4$alkoxy-substituted $C_3$–$C_8$cycloalkylene, unsubstituted or $C_1$–$C_4$alkyl- or $C_1$–$C_4$alkoxy-substituted $C_3$–$C_8$cycloalkylene-$C_yH_{2y}$- or unsubstituted or $C_1$–$C_4$alkyl- or $C_1$–$C_4$alkoxy-substituted-$C_yH_{2y}$-($C_3$–$C_8$cycloalkylene)-$C_yH_{2y}$—;

$R_5$ independently has the same definitions as $R_4$ or is linear $C_3$–$C_{18}$alkylene;

$R_{1A}$ is lower alkyl;

x is an integer from 3 to 5;

y is an integer from 1 to 6;

$R_a$ and $R_b$ are each independently of the other H, $C_1$–$C_8$alkyl, $C_3$–$C_8$cycloalkyl, benzyl or phenyl;

with the provisos that n in the groups —$(Y_1)_n$—$R_1$ is 0 when $R_2$ is H; that not more than two $Y_1$ of the —$(Y_1)_n$— groups are 0 and n in the other —$(Y_1)_n$— groups is 0; and that n in the group —$(Y_2)_n$— is 0 when $R_3$ is a direct bond;

and wherein also X is bivalent —O—, —NH—, —S—, lower alkylene or

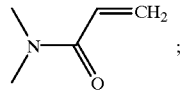

$Y_{10}$ is a direct bond or —O—$(CH_2)_y$— wherein y is an integer from 1 to 6 and the terminal $CH_2$ group of which is linked to the adjacent X in formula (Ib);

$R_{100}$ is H, $C_1$–$C_{12}$alkyl, $C_1$–$C_{12}$alkoxy, $C_1$-CalkylNH— or —$NR_{1A}R_{1B}$ wherein $R_{1A}$ is lower alkyl and $R_{1B}$ is H or lower alkyl;

$R_{101}$, is linear or branched lower alkyl, lower alkenyl or aryl-lower alkyl;

$R_{102}$ independently of $R_{101}$, has the same definitions as $R_{101}$, or is aryl, or $R_{101}$, and $R_{102}$ together are, —$(CH_2)_m$— wherein m is an integer from 2 to 6;

$R_{103}$ and $R_{104}$ are each independently of the other linear or branched lower alkyl that may be substituted by $C_1$–$C_4$alkoxy, or aryl-lower alkyl or lower alkenyl; or $R_{103}$ and $R_{104}$ together are —$(CH_2)_z$—$Y_{11}$—$(CH_2)_z$— wherein $Y_{11}$ is a direct bond, —O—, —S— or —$NR_{1B}$—, and $R_{1B}$ is H or lower alkyl and each z independently of the other is an integer from 2 to 4.

15. A contact lens comprising (a) a transparent organic base material and (b) a covalenty bonded thin layer on the surface, consisting of (b1) constituents that are derived from at least one photoinitiator of formula Ia or Ib and (b2) a polymer of an olefin that is covalenty bonded to isocyanate groups of constituent (b1) via groups that are co-reactive with isocyanate groups, wherein formulae Ia and Ib are as follows:

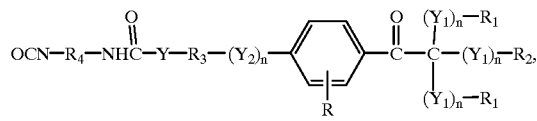
(Ia)

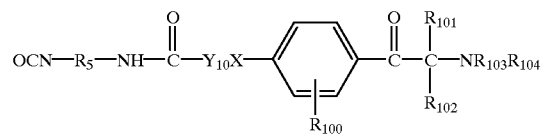
(Ib)

wherein Y is O, NH or $NR_{1A}$;

$Y$, is O;

$Y_2$ is —O—, —O—(O)C—, —C(O)—O— or —O—C(O)—O—;

each n independently of the others is 0 or 1;

R is H, $C_1$–$C_{12}$alkyl, $C_1$–$C_{12}$alkoxy or $C_1$–$C_2$alkylNH—;

$R_1$ and $R_2$ are each independently of the other H, linear or branched $C_1$–$C_8$alkyl, $C_1$–$C_8$hydroxyalkyl or $C_6$–$C_{10}$aryl, or two groups $R_1$—$(Y_1)_n$— together are —$(CH_2)_x$—, or the groups $R_1$—$(Y_1)_n$— and $R_2$—$(Y_1)_n$— together are a radical of the formula

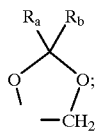

$R_3$ is a direct bond or linear or branched $C_1$–$C_8$alkylene that is unsubstituted or substituted by —OH and/or optionally interrupted by one or more groups —O—, —O—C(O)— or —O—C(O)—O—;

$R_4$ is branched $C_3$–$C_{18}$alkylene, unsubstituted or $C_1$–$C_4$alkyl- or $C_1$–$C_4$alkoxy-substituted $C_6$–$C_{10}$arylene, or unsubstituted or $C_1$–$C_4$alkyl- or $C_1$–$C_4$alkoxy-substituted $C_7$–$C_{18}$-aralkylene, unsubstituted or $C_1$–$C_4$alkyl- or $C_1$–$C_4$alkoxy-substituted $C_3$–$C_8$cycloalkylene, unsubstituted or $C_1$–$C_4$alkyl- or $C_1$–$C_4$alkoxy-substituted $C_3$–$C_8$cycloalkylene-$C_yH_{2y}$- or unsubstituted or $C_1$–$C_4$alkyl- or $C_1$–$C_4$alkoxy-substituted-$C_yH_{2y}$-($C_3$–$C_8$cycloalkylene)-$C_yH_{2y}$—;

$R_5$ independently has the same definitions as $R_4$ or is linear $C_3$–$C_{18}$alkylene;

$R_{1A}$ is lower alkyl;

x is an integer from 3 to 5;

y is an integer from 1 to 6;

$R_a$ and $R_b$ are each independently of the other H, $C_1$–$C_8$alkyl, $C_3$–$C_8$cycloalkyl, benzyl or phenyl;

with the provisos that n in the groups —$(Y_1)_n$—$R_1$ is 0 when $R_2$ is H; that not more than two $Y_1$ of the —$(Y_1)_n$— groups are 0 and n in the other —$(Y_1)_n$— groups is 0; and that n in the group —$(Y_2)_n$— is 0 when $R_3$ is a direct bond;

and wherein also X is bivalent —O—, —NH—, —S—, lower alkylene or

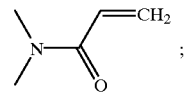

$Y_{10}$ is a direct bond or —O—$(CH_2)y$— wherein y is an integer from 1 to 6 and the terminal $CH_2$ group of which is linked to the adjacent X in formula (Ib);

$R_{100}$ is H, $C_1$–$C_{12}$alkyl, $C_1$–$C_{12}$alkoxy, $C_1$-CalkylNH— or —$NR_{1A}R_{1B}$ wherein $R_{1A}$ is lower alkyl and $R_{1B}$ is H or lower alkyl;

$R_{101}$, is linear or branched lower alkyl, lower alkenyl or aryl-lower alkyl;

$R_{102}$ independently of $R_{101}$, has the same definitions as $R_{101}$, or is aryl, or $R_{101}$, and $R_{102}$ together are, —$(CH_2)_m$— wherein m is an integer from 2 to 6;

$R_{103}$ and $R_{104}$ are each independently of the other linear or branched lower alkyl that may be substituted by $C_1$–$C_4$alkoxy, or aryl-lower alkyl or lower alkenyl; or $R_{103}$ and $R_{104}$ together are —$(CH_2)_z$—$Y_{11}$—$(CH_2)_z$— wherein $Y_{11}$ is a direct bond, —O—, —S— or —$NR_{1B}$—, and $R_{1B}$ is H or lower alkyl and each z independently of the other is an integer from 2 to 4.

16. A film comprising (a) a base material and (b) a covalently bonded thin layer on the surface, consisting of (b) constituents that are derived from at least one photoinitiator of formula Ia or Ib, the constituents (b) still containing isocyanate groups in free form, wherein formulae Ia and Ib are as follows:

(Ia)

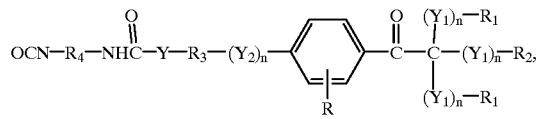

(Ib)

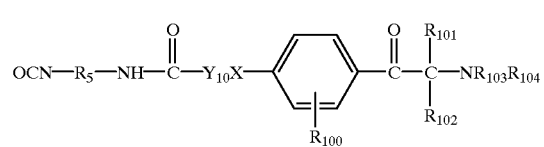

wherein Y is O, NH or $NR_{1A}$;

$Y_1$ is O;

$Y_2$ is —O—, —O—(O)C—, —C(O)—O— or —O—C(O)—O—;

each n independently of the others is 0 or 1;

R is H, $C_1$–$C_{12}$alkyl, $C_1$–$C_{12}$alkoxy or $C_1$–$C_{12}$alkylNH—;

$R_1$ and $R_2$ are each independently of the other H, linear or branched $C_1$–$C_8$alkyl, $C_1$–$C_8$hydroxyalkyl or $C_6$–$C_{10}$aryl, or two groups $R_1$—$(Y_1)_n$— together are —$(CH_2)_x$—, or the groups $R_1$—$(Y_1)_n$— and $R_2$—$(Y_1)_n$— together are a radical of the formula

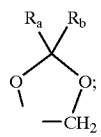

$R_3$ is a direct bond or linear or branched $C_1$–$C_8$alkylene that is unsubstituted or substituted by —OH and/or optionally interrupted by one or more groups —O—, —O—C(O)— or —O—C(O)—O—;

$R_4$ is branched $C_3$–$C_{18}$alkylene, unsubstituted or $C_1$–$C_4$alkyl- or $C_1$–$C_4$alkoxy-substituted $C_6$–$C_{10}$arylene, or unsubstituted or $C_1$–$C_4$alkyl- or $C_1$–$C_4$alkoxy-substituted $C_7$–$C_{18}$-aralkylene, unsubstituted or $C_1$–$C_4$alkyl- or $C_1$–$C_4$alkoxy-substituted $C_3$–$C_8$cycloalkylene, unsubstituted or $C_1$–$C_4$alkyl- or $C_1$–$C_4$alkoxy-substituted $C_3$–$C_8$cycloalkylene-$C_yH_{2y}$- or unsubstituted or $C_1$–$C_4$alkyl- or $C_1$–$C_4$alkoxy-substituted-$C_yH_{2y}$-($C_3$–$C_8$cycloalkylene)-$C_yH_{2y}$—;

$R_5$ independently has the same definitions as $R_4$ or is linear $C_3$–$C_{18}$alkylene;

$R_{1A}$ is lower alkyl;

x is an integer from 3 to 5;

y is an integer from 1 to 6;

$R_a$ and $R_b$ are each independently of the other H, $C_1$–$C_8$alkyl, $C_3$–$C_8$cycloalkyl, benzyl or phenyl;

with the provisos that n in the groups —$(Y_1)_n$—$R_1$ is 0 when $R_2$ is H; that not more than two $Y_1$ of the —$(Y_1)_n$— groups are 0 and n in the other —$(Y_1)_n$— groups is 0; and that n in the group —$(Y_2)_n$— is 0 when $R_3$ is a direct bond;

and wherein also X is bivalent —O—, —NH—, —S—, lower alkylene or

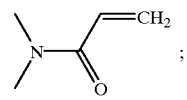

$Y_{10}$ is a direct bond or —O—$(CH_2)_y$— wherein y is an integer from 1 to 6 and the terminal $CH_2$ group of which is linked to the adjacent X in formula (Ib);

$R_{100}$ is H, $C_1$–$C_{12}$alkyl, $C_1$–$C_{12}$alkoxy, $C_1$-CalkylNH— or —$NR_{1A}R_{1B}$ wherein $R_{1A}$ is lower alkyl and $R_{1B}$ is H or lower alkyl;

$R_{101}$, is linear or branched lower alkyl, lower alkenyl or aryl-lower alkyl;

$R_{102}$ independently of $R_{101}$, has the same definitions as $R_{101}$, or is aryl, or $R_{101}$, and $R_{102}$ together are, —$(CH_2)_m$— wherein m is an integer from 2 to 6;

$R_{103}$ and $R_{104}$ are each independently of the other linear or branched lower alkyl that may be substituted by $C_1$–$C_4$alkoxy, or aryl-lower alkyl or lower alkenyl; or $R_{103}$ and $R_{104}$ together are —$(CH_2)_z$—$Y_{11}$—$(CH_2)_z$— wherein $Y_{11}$ is a direct bond, —O—, —S— or —$NR_{1B}$—, and $R_{1B}$ is H or lower alkyl and each z independently of the other is an integer from 2 to 4.

17. A contact lens comprising (a) a transparent organic base material and (b) a covalently bonded thin layer on the surface, consisting of (b) constituents that are derived from at least one photoinitiator of formula Ia or Ib, the constituents (b) still containing isocyanate groups in free form, wherein formulae Ia and Ib are as follows:

(Ia)

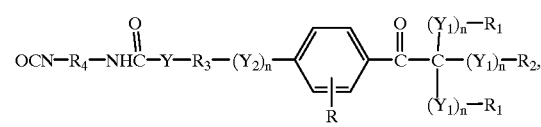

(Ib)

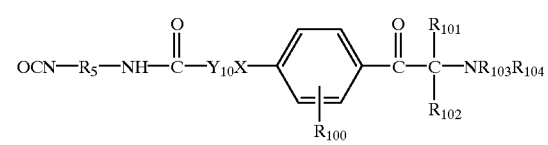

wherein Y is O, NH or $NR_{1A}$;

$Y_1$ is O;

$Y_2$ is —O—, —O—(O)C—, —C(O)—O— or —O—C(O)—O—;

each n independently of the others is 0 or 1;

R is H, $C_1$–$C_{12}$alkyl, $C_1$–$C_{12}$alkoxy or $C_1$–$C_{12}$alkylNH—;

$R_1$ and $R_2$ are each independently of the other H, linear or branched $C_1$–$C_8$alkyl, $C_1$–$C_8$hydroxyalkyl or $C_6$–$C_{10}$aryl, or two groups $R_1$—$(Y_1)_n$— together are —$(CH_2)_x$—, or the groups $R_1$—$(Y_1)_n$— and $R_2$—$(Y_1)_n$— together are a radical of the formula

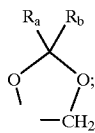

$R_3$ is a direct bond or linear or branched $C_1$–$C_8$alkylene that is unsubstituted or substituted by —OH and/or optionally interrupted by one or more groups —O—, —O—C(O)— or —O—C(O)—O—;

$R_4$ is branched $C_3$–$C_{18}$alkylene, unsubstituted or $C_1$–$C_4$alkyl- or $C_1$–$C_4$alkoxy-substituted $C_6$–$C_{10}$arylene, or unsubstituted or $C_1$–$C_4$alkyl- or $C_1$–$C_4$alkoxy-substituted $C_7$–$C_{18}$-aralkylene, unsubstituted or $C_1$–$C_4$alkyl- or $C_1$–$C_4$alkoxy-substituted $C_3$–$C_8$cycloalkylene, unsubstituted or $C_1$–$C_4$alkyl- or $C_1$–$C_4$alkoxy-substituted $C_3$–$C_8$cycloalkylene-$C_yH_{2y}$- or unsubstituted or $C_1$–$C_4$alkyl- or $C_1$–$C_4$alkoxy-substituted-$C_yH_{2y}$-($C_3$–$C_8$cycloalkylene-$C_yH_{2y}$—;

$R_5$ independently has the same definitions as $R_4$ or is linear $C_3$–$C_{18}$alkylene;

$R_{1A}$ is lower alkyl;

x is an integer from 3 to 5;

y is an integer from 1 to 6;

$R_a$ and $R_b$ are each independently of the other H, $C_1$–$C_8$alkyl, $C_3$–$C_8$cycloalkyl, benzyl or phenyl;

with the provisos that n in the groups —$(Y_1)_n$—$R_1$ is 0 when $R_2$ is H; that not more than two $Y_1$ of the —$(Y_1)_n$— groups are 0 and n in the other —$(Y_1)_n$— groups is 0; and that n in the group —$(Y_2)_n$— is 0 when $R_3$ is a direct bond;

and wherein also X is bivalent —O—, —NH—, —S—, lower alkylene or

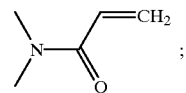

$Y_{10}$ is a direct bond or —O—$(CH_2)y$— wherein y is an integer from 1 to 6 and the terminal $CH_2$ group of which is linked to the adjacent X in formula (Ib);

$R_{100}$ is H, $C_1$–$C_{12}$alkyl, $C_1$–$C_{12}$alkoxy, $C_1$-CalkylNH— or —$NR_{1A}R_{1B}$ wherein $R_{1A}$ is lower alkyl and $R_{1B}$ is H or lower alkyl;

$R_{101}$, is linear or branched lower alkyl, lower alkenyl or aryl-lower alkyl;

$R_{102}$ independently of $R_{101}$, has the same definitions as $R_{101}$, or is aryl, or $R_{101}$, and $R_{102}$ together are, —$(CH_2)_m$— wherein m is an integer from 2 to 6;

$R_{103}$ and $R_{104}$ are each independently of the other linear or branched lower alkyl that may be substituted by $C_1$–$C_4$alkoxy, or aryl-lower alkyl or lower alkenyl; or $R_{103}$ and $R_{104}$ together are —$(CH_2)_z$—$Y_{11}$—$(CH_2)_z$— wherein $Y_{11}$ is a direct bond, —O—, —S— or —$NR_{1B}$—, and $R_{1B}$ is H or lower alkyl and each z independently of the other is an integer from 2 to 4.

\* \* \* \* \*